US007241743B2

(12) United States Patent
Gu et al.

(10) Patent No.: US 7,241,743 B2
(45) Date of Patent: Jul. 10, 2007

(54) SIR2α-BASED THERAPEUTIC AND PROPHYLACTIC METHODS

(75) Inventors: Wei Gu, New York, NY (US); Jian Yuan Luo, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 116 days.

(21) Appl. No.: 10/172,706

(22) Filed: Jun. 14, 2002

(65) Prior Publication Data

US 2003/0124101 A1 Jul. 3, 2003

Related U.S. Application Data

(60) Provisional application No. 60/298,506, filed on Jun. 15, 2001.

(51) Int. Cl.
*A01N 43/04* (2006.01)
(52) U.S. Cl. ...................................................... 514/44
(58) Field of Classification Search .................... 514/44
See application file for complete search history.

(56) References Cited

U.S. PATENT DOCUMENTS

| 4,690,918 A | 9/1987 | Beppu et al. |
| 2002/0183388 A1 | 12/2002 | Gudas et al. |
| 2003/0207325 A1* | 11/2003 | Guarente et al. ............ 435/7.1 |

OTHER PUBLICATIONS

The Merck Manual of Diagnosis and Therapy, 15th edtion. Berkow, Editor. (1987) (Merck Sharp and Dohme Research Laboratories: Rahway, NJ) p. 930-931 and 944.*
Juengst, E. "What next for human gene therapy? Gene transfer often has multiple and unpredicatable effects on cells" British Med. J. (2003) 326(7404): 1410-1411.*
Tsukamoto et al. "Silencing factors participate in DNA repair and recombination in *Saccharomyces cerevisiae*" Nature (1997) 388: 900-903.*
Olsson et al. "DNA damage and repair in tumor and non-tumor tissues of mice indused by nicotinamide" Br. J. Cancer (1996) 74:368-373.*
Jenkins et al. "Virtual Screening to Enrich Hit Lists from High-Throughput Screening: A Case Study on Small-Molecule Inhbitors of Angiogenin" Proteins:Strucutre, Function and Genetics (2003) 50: 81-93.*
Ginalski et al. "Practical Lessons from Protein Structure Prediction" Nucleic Acids Res. (2005) 33(6): 1874-1891.□□.*
Langley, E., et al., "Human SIR2 Deacetylates p53 and Antagonizes PML/p53-Induced Cellular Senescence." The EMBO Journal. vol. 21, No. 10, 2383-2396 (2002) (Exhibit 5).
Luo, J., et al., "Negative Control of p53 Sir2 Alpha Promotes Cell Survival Under Stress." Cell. vol. 107, No. 2, 137-148 (2001) (Exhibit 6).
Vaziri, H., et al., "hSIR2$^{SIRT1}$ Functions as an NAD-Dependent p53 Deacetylase." Cell. vol. 107, 149-159 (2001) (Exhibit 7).
Appella, E., et al., "Signaling to p-53: Breaking the Posttranslational Modification Code." Pathol. Biol. (Paris) 48, 227-245 (2000) (Exhibit 1).
Avantaggiati, M.L., et al., "Recruitment of p300/CBP in p53-Dependent Signal Pathways." Cell 89, 1175-1184 (1997) (Exhibit 2).

Bernstein, B.E., et al. "Genomewide Studies of Histone Deacetylase Function in Yeast." Proc. Natl. Acad. Sci. USA, 97, 13708-13713 (2000) (Exhibit 3).
Butler, L.M., et al., "Suberoylanilide Hydroxamic Acid, an Inhibitor of Histone Deacetylase, Suppresses the Growth of Prostate Cancer cells *in Vitro* and *In Vivo*." Cancer Res. 60, 5165-5170 (2000) (Exhibit 4).
Campisi, J., "Aging, Chromatin, and Food Restriction—Connecting the Dots." Science 289, 2062-2063 (2000) (Exhibit 5).
Chao, Q.M., et al., "p53 Transcriptional Activity is Essential for p53-dependent Apoptosis Following DNA Damage." EMBO J. 19, 4967-4975 (2000) (Exhibit 6).
Chen, Q.M., et al., "Apoptosis or Senescence-Like Growth Arrest: Influence of Cell-Cycle Position, p53, p21 and bax in $H_2O_2$ Response of Normal Human Fibroblasts." Biochem. J. 347, 543-551 (2000) (Exhibit 7).
Chresta, C.M., et al., "Oddball p53 in Testicular Tumors." Nat. Med. 2, 745-746 (1996) (Exhibit 8).
Di Cristofano, A., et al. "Impaired Fas Response and Autoimmunity in *Pten+/ –* Mice." Science 285 , 2122-2125 (1999) (Exhibit 9).
Ferbeyre, G., et al., "PML is Induced by Oncogenic RAS and Promotes Premature Senescence." Genes Dev. 14 , 2015-2027 (2000) (Exhibit 10).
Finnin, M.S., et al., "Structure of the Histone Deacetylase SIRT2." Nat. Struct. Biol. 8, 621-625 (2001) (Exhibit 11).
Freedman, D.A., et al., "Functions of the MDM2 Oncoprotein. Cell Mol." Life Sci. 55, 96-107 (1999) (Exhibit 12).
Frye, R.A., "Characterization of Five Human cDNAs with Homology to the Yeast SIR2 Gene: Sir2-like Proteins (Sirtuins) Metabolize NAD and May Have Protein ADP-Ribosyltransferase Activity." Biochem. Biophys. Res. Commun. 260 , 273-279 (1999) (Exhibit 13).
Frye, R.A., "Phylogenetic Classification of Prokaryotic and Eukaryotic Sir2-like Proteins." Biochem. Biophys. Res. Commun. 273 , 793-798 (2000) (Exhibit 14).
Gu, W., et al., "Activation of p53 Sequence-Specific DNA Binding by Acetylation of the p53 C-Terminal Domain." Cell 90, 595-606 (1997) (Exhibit 15).

(Continued)

*Primary Examiner*—Leon B. Lankford
*Assistant Examiner*—Susan Hanley
(74) *Attorney, Agent, or Firm*—John P. White; Cooper & Dunham LLP

(57) ABSTRACT

This invention provides methods for treating and for inhibiting the onset of cancer in a subject comprising administering an agent that inhibits the ability of Sir2α to inhibit p53-dependent apoptosis. This invention also provides a related method for inducing the death of a cell. This invention further provides a method for decreasing the amount of damage to a subject's cells caused by physical stress comprising administering agent that increases the amount of Sir2α in the subject's cells and/or the ability of Sir2α to inhibit p53-dependent apoptosis in the subject's cells. This invention further provides related methods for prolonging the life-span of a subject, decreasing the amount of damage to a cell caused by physical stress, and prolonging the life-span of a cell. Finally, this invention provides two articles of manufacture for performing the instant methods.

8 Claims, 30 Drawing Sheets

OTHER PUBLICATIONS

Gu, W., et al., "A Novel Human SRB/MED-Containing Cofactor Complex, SMC, Involved in Transcriptase Regulation." Mole Cell 3, 97-108 (1999) (Exhibit 16).

Gu, W., et al., "Synergistic Activation of Transcription by CBP and p53." Nature 387, 819-823 (1997) (Exhibit 17).

Guarente, L., "Sir2 links Chromatin Silencing, Metabolism, and Aging." Genes Dev. 14, 1021-1026 (2000) (Exhibit 18).

Guo, A., et al., "The Function of PML in p53-dependent Apoptosis." Nature Cell Biol. 2, 730-736 (2000) (Exhibit 19).

Hollstein, M., et al., "Database of p53 Gene Somatic Mutations in Human Tumors and Cell Lines." Nucleic Acids Res 22, 3551-3555 (1994) (Exhibit 20).

Imai, S., et al., "Transcriptional Silencing and Longevity Protein Sir2 is an NAD-dependent Histone Deacetylase." Nature 403, 795-800 (2000) (Exhibit 21).

Ito, A., et al., "p300/CBP-mediated p53 Acetylation is Commonly Induced by p53-activating Agents and Inhibited by MDM2." EMBO J. 20, 1331-1340 (2001) (Exhibit 22).

Jimenez, G.S., et al., "A Transactivation-Deficient Mouse Model Provides Insights Into Trp53 Regulation and Function." Nature Genetics 26, 37-43 (2000) (Exhibit 23).

Juan, L.J., et al., "Histone Deacetylases Specifically Down-Regulate p53-dependent Gene Activation." J. Bio. Chem. 275, 20436-20443 (2000) (Exhibit 24).

Kaeberlein, M., et al., "The SIR2/3/4 Complex and SIR2 Alone Promote Longevity in *Saccharomyces cerevisiae* by Two Different Mechanisms." Genes Dev. 13, 2570-2580 (1999) (Exhibit 25).

Kobet, E., et al., "MDM2 Inhibits p300-mediated p53 Acetylation and Activation by Forming a Ternary Complex with the Two Proteins." Proc. Natl. Acad. Sci. U.S.A 97, 12547-12552 (2000) (Exhibit 26).

Kouzarides, T., "Acetylation: A Regulatory Modification to Rival Phosphorylation?" EMBO. J. 19 1176-1179 (2000) (Exhibit 27).

Kuo, M.H. et al., "Roles of Histone Acetyltransferases and Deacetylases in Gene Regulation." Bioessays 20, 615-626 (1998) (Exhibit 28).

Landry, J., et al., "Role of NAD+ in the Deacetylase Activity of the SIR2-like Proteins." Biochem. Biophys. Res. Commun. 278. 685-690 (2000) (Exhibit 29).

Landry, J., et al., "The Silencing Protein SIR2 and its Homologs are NAD-Dependent Protein Deacetylases." Proc. Natl. Acad. Sci. U.S.A. 97, 5807-5811 (2000) (Exhibit 30).

Levine, A.J., "p53, the Cellular Gatekeeper for Growth and Division." Cell 88, 323-331 (1997) (Exhibit 31).

Lill, N.L., et al., "Binding and Modulation of p53 by p300/CBP Coactivators." Nature 387, 823-827 (1997) (Exhibit 32).

Lin, S.J., et al., "Requirement of NAD and SIR2 for Life-Span Extension by Calorie Restriction in *Saccharomyces cerevisiae*." Science 289, 2126-2128 (2000) (Exhibit 33).

Liu, L., et al., "p53 Sites Acetylated In Vitro by PCAF and p300 Are Acetylated In Vivo in Response to DNA Damage." Mol. Cell Biol. 19, 1202-1209 (1999) (Exhibit 34).

Lohrum, M.A., et al., "Regulation and Activation of p53 and its Family Members." Cell Growth Differ. 6, 1162-1168 (1999) (Exhibit 35).

Luo, J., et al., "Deacetylation of p53 Modulates its Effect on Cell Growth and Apoptosis." Nature 408, 377-381 (2000) (Exhibit 36).

Lutzker, S.G., et al., "A Functionally Inactive p53 Protein in Teratocarcinoma Cells is Activated by Either DNA Damage or Cellular Differentiation." Nat. Med. 2, 804-810 (1996) (Exhibit 37).

Marks, P.A., et al., "Inhibitors of Histone Deacetylase Are Potentially Effective Anticancer Agents." Clin. Cancer Res. 7, 759-760 (2001) (Exhibit 38).

Maya, R., et al., "ATM-Dependent Phosphorylation of Mdm2 on Serine 395: Role in p53 Activation by DNA Damage." Genes Dev. 15, 1067-1077 (2001) (Exhibit 39).

Migliaccio, E., et al., The p66$^{shc}$ Adaptor Protein Controls Oxidative Stress Response and Life Span in Mammals. Nature 402, 309-313 (1999) (Exhibit 40).

Min, J., et al., "Crystal Structure of a SIR2 Homolog-NAD Complex." Cell 105, 269-279 (2001) (Exhibit 41).

Muth, V., et al., "Acetylation of TAF$_I$68, A Subunit of TIF-IB/SL1, Activates RNA Polymerase I Transcription."EMBO J. 20, 1353-1362 (2001) (Exhibit 42).

Nakamura, S., et al., "Multiple Lysine Mutations in the C-Terminal Domain of p53 Interfere with MDM2-Dependent Protein Degradation and Ubiquitination."Mol. Cell Biol. 20, 9391-9398 (2000) (Exhibit 43).

Nakano, K., et al., "*PUMA*, a Novel Proapoptotic Gene, is Induced by p53." Molecular Cell 7, 683-694 (2001) (Exhibit 44).

Pearson, M., et al., "PML Regulates p53 Acetylation and Premature Senescence Induced by Oncogenic Ras." Nature 406, 207-210 (2000) (Exhibit 45).

Perrod, S., et al., "A Cytosolic NAD-dependent Deacetylase Hst2p, can Modulate Nucleolar and Telomeric Silencing in Yeast." EMBO J. 20, 197-209 (2001) (Exhibit 46).

Prives, C., et al., "The P53 Pathway." Pathol. J. 187, 112-126 (1999) (Exhibit 47).

Rodriguez, M., et al. "Multiple C-Terminal Lysine Residues Targer p53 for Ubiquitin-Proteasome-Mediated Degradation." Mol. Cell Biol. 20, 8548-8467 (2000) (Exhibit 48).

Sakaguchi, K., et al., "DNA Damage Activates p53 Through a Phosphorylation-Acetylation Cascade." Genes Dev. 12, 2831-2841 (1998) (Exhibit 49).

Shieh, S.Y., et al., "DNA Damage-Induced Phosphorylation of p53 Alleviates Inhibition by MDM2." Cell 91, 325-334 (1997) (Exhibit 50).

Shore, D., "The Sir2 Protein Family: A Novel Deacetylase for Gene Silencing and More." Proc. Natl. Acad. Sci. U.S.A. 97, 14030-14032 (2000) (Exhibit 51).

Smith, J.S., et al., "A Phylogenetically Conserved NAD$^+$-dependent Protein Deacetylase Activity in the Sir2 Protein Family." Proc. Natl. Acad. Sci. U.S.A 97, 6658-6663 (2000) (Exhibit 52).

Sterner, D.E., et al., "Acetylation of Histones and Transcription-Related Factors." Microbiol. Mol. Biol. 64, 435-459 (2000) (Exhibit 53).

Tanner, K.G., et al., "Silent Information Regulator 2 Family of NAD-Dependent Histone/Protein Deacetylases Generates a Unique Product, 1-*O*-acetyl-ADP-ribose." Proc. Natl. Acad. Sci. U.S.A. 97, 14178-14182 (2000) (Exhibit 54).

Tanny, J.C., et al., Coupling of Histone Deacetylation to NAD Breakdown by the Yeast Silencing Protein Sir2: Evidence for Acetyl Transfer from Substrate to an NAD Breakdown Product. Proc. Natl. Acad. Sci. U.S.A. 98, 415-420 (2001) (Exhibit 55).

Tissenbaum, H.A., et al., "Increased Dosage of a *sir-2* Gene Extends Lifespan in *Caenorhabditis elegans*." Nature 410, 227-230 (2001) (Exhibit 56).

Vaziri, H., et al., ATM-Dependent Telomere Loss in Aging Human Diploid Fibroblasts and DAN damage Lead to the Post-Translational Activation of p53 Protein Involving Poly (ADP-ribose) Polymerase. EMBO. J. 16, 6018-6033 (1997) (Exhibit 57).

Vogelstein, B., et al., "Surfing the p53 Network." Nature 408, 307-310 (2000) (Exhibit 58).

Yang, Y., et al., "Cloning and Characterization of Two Mouse Genes with Homology to the Yeast *Sir2* Gene." Genomics 69, 355-369 (2000) (Exhibit 59).

Yin, Y., et al., "Involvement of p85 in p53-dependent Apoptotic Response to Oxidative Stress." Nature 391, 707-710 (1998) (Exhibit 60).

Yoshida, M., et al., "Trichostatin A and Trapoxin: Novel Chemical Probes for the Role of Histone Acetylation in Chromatin Structure and Function." Bioessays 5, 423-430 (1995) (Exhibit 61).

Yu, A., et al., "Activation of p53 or Loss of the Cockayne Syndrome Group B Repair Protein Causes Metaphase Fragility of Human U1, U2, 5S Genes." Mol. Cell 5, 801-810 (2000) (Exhibit 62).

Yu, J., et al., "PUMA Induces the Rapid Apoptosis of Colorectal Cancer Cells." Molecular Cell 7, 673-682 (2001) (Exhibit 63).

* cited by examiner

SIR2α-BASED THERAPEUTIC AND PROPHYLACTIC METHODS

This application claims the benefit of U.S. Provisional Application No. 60/298,506, filed Jun. 15, 2001, the contents of which are hereby incorporated by reference into this application.

BACKGROUND OF THE INVENTION

The p53 tumor suppressor exerts anti-proliferative effects, including growth arrest, apoptosis, and cell senescence, in response to various types of stress (Levine, 1997; Prives and Hall, 1999; Vogelstein et al., 2000). Mutations within the p53 gene have been well documented in more than half of all human tumors (Hollstein et al., 1994). Accumulating evidence further indicates that, in the cells that retain wild-type p53, other defects in the p53 pathway also play an important role in tumorigenesis (Prives and Hall, 1999; Lohrum and Vousden, 1999). The molecular function of p53 that is required for tumor suppression involves its ability to act as a transcriptional factor in regulating downstream target gene expression (reviewed in Nakano and Vousden, 2001; Yu et al., 2001).

p53 is a short-lived protein whose activity is maintained at low levels in normal cells. Tight regulation of p53 is essential for its effect on tumorigenesis as well as maintaining normal cell growth. The precise mechanism by which p53 is activated by cellular stress is not completely understood; it is generally thought to involve mainly post-translational modifications of p53, including phosphorylation and acetylation (reviewed in Appella and Anderson, 2000). Early studies demonstrated that CBP/p300, a histone acetyl-transferase (HAT), acts as a coactivator of p53 and potentiates its transcriptional activity as well as biological function in vivo (Gu et al., 1997; Lill et al., 1997; Avantaggiati et al., 1997). Significantly, the observation of functional synergism between p53 and CBP/p300 together with its intrinsic HAT activity led to the discovery of a novel FAT (transcriptional factor acetyl-transferase) activity of CBP/p300 on p53. This finding also indicates that acetylation may represent a general functional modification for non-histone proteins in vivo (Gu and Roeder, 1997).

Through the use of site-specific acetylated p53 antibodies, CBP/p300 mediated acetylation of p53 was further confirmed in vivo by a number of studies (Sakaguchi et al., 1998; Liu et al., 1999; Luo et al., 2000; Kobet et al., 2000; Ito et al., 2001). Significantly, the steady-state levels of acetylated p53 are stimulated in response to various types of stress, indicating the important role of p53 acetylation in stress response (reviewed in Ito et al., 2001).

By introducing a transcriptionally defective p53 mutant ($p53^{Q25S26}$) into mice, it was found that the mutant mouse thymocytes and ES cells failed in undergoing DNA damage-induced apoptosis (Chao et al., 2000; Jimenez et al., 2000). Interestingly, this mutant protein was phosphorylated normally at the N-terminus in response to DNA damage but could not be acetylated at the C-terminus (Chao et al., 2000), supporting a critical role of p53 acetylation in p53-dependent apoptotic response (Chao et al., 2000; Luo et al., 2000).

Furthermore, it has been found that oncogenic Ras as well as PML can upregulate the levels of acetylated p53 in normal primary fibroblasts, and also induce premature senescence in a p53-dependent manner (Pearson et al., 2000; Ferbeyre et al., 2000). p53 acetylation may also play a critical role in protein stabilization (Rodriguez et al., 2000; Nakamura et al., 2000; Ito et al., 2001). In addition, another independent study showed that acetylation, but not phosphorylation of the p53 C-terminus, may be required to induce metaphase chromosome fragility in the cell (Yu et al., 2000).

In contrast, much less is known about the role of deacetylation in modulating p53 function. The acetylation level of p53 is enhanced when the cells are treated with histone deacetylase (HDAC) inhibitors such as Trichostatin A (TSA). This observation led to the identification of a HDAC1 complex which is directly involved in p53 deacetylation and functional regulation (Luo et al., 2000; Juan et al., 2000).

PID/MTA2, a metastasis-associated protein 2, acts as an adaptor protein to enhance HDAC1-mediated deacetylation of p53, but this activity can be completely repressed by TSA (Luo et al., 2000). In addition, Mdm2, a negative regulator of p53, actively suppresses CBP/p300-mediated p53 acetylation, and this inhibitory effect can be abrogated by tumor suppressor $p19^{ARF}$, suggesting that regulation of acetylation also plays a critical role in the p53-MDM2-$p19^{ARF}$ feed back loop (Ito et al., 2001; Kobet et al., 2000).

The yeast silent information regulator 2 (Sir2) protein belongs to a novel family of histone deacetylases (reviewed in Guarente, 2000; Shore, 2000). Sir2 activity is nicotinamide adenine dinucleotide (NAD)-dependent, but can not be inhibited by TSA (Imai et al., 2000; Landry et al., 2000a; Smith et al., 2000). The NAD-dependent deacetylase activity of Sir2 is essential for its functions, and this activity also connects its biological role with cellular metabolism in yeast (Guarente, 2000; Imai et al., 2000; Lin et al., 2000; Smith et al., 2000). Recently, mammalian Sir2 homologs have been found to also contain the NAD-dependent histone deacetylase activity (Imai et al., 2000; Smith et al., 2000), further supporting the notion that the enzymatic activity is key to elucidating the molecular mechanism for its mediated functions (Min et al., 2001; Finnin et al., 2001).

Among Sir2 and its homolog proteins (HSTs) in yeast, Sir2 is the only protein exclusively localized in nuclei, whose activity is critical for both gene silencing and extension of yeast life-span (reviewed in Guarente, 2000). Based on protein sequence homology analysis, mouse Sir2α and its human ortholog SIRT1 (or human Sir2α) are the closest homologs to yeast Sir2 (Imai et al., 2000; Frye, 1999, 2000). However, their biological functions remain unclear.

SUMMARY OF THE INVENTION

This invention provides a method for treating a subject afflicted with cancer comprising administering to the subject a therapeutically effective amount of an agent that inhibits the ability of Sir2α to inhibit p53-dependent apoptosis, thereby treating the subject.

This invention also provides a method for inhibiting the onset of cancer in a subject comprising administering to the subject a prophylactically effective amount of an agent that inhibits the ability of Sir2α to inhibit p53-dependent apoptosis, thereby inhibiting the onset of cancer in the subject.

This invention further provides a method for inducing the death of a cell comprising contacting the cell with an agent that inhibits the ability of Sir2α to inhibit p53-dependent apoptosis, thereby inducing the death of the cell.

This invention further provides a method for decreasing the amount of damage to a subject's cells caused by physical stress comprising administering to the subject a prophylactically effective amount of an agent that increases the amount of Sir2α in the subject's cells and/or the ability of Sir2α to inhibit p53-dependent apoptosis in the subject's cells, thereby decreasing the amount of damage to the subject's cells.

This invention further provides a method for prolonging the life-span of a subject comprising administering to the subject a prophylactically effective amount of an agent that increases the amount of Sir2α in the subject's cells and/or the ability of Sir2α to inhibit p53-dependent apoptosis in the subject's cells, thereby prolonging the subject's life-span.

This invention further provides a method for decreasing the amount of damage to a cell caused by physical stress comprising contacting the cell with an agent that increases the amount of Sir2α in the cell and/or the ability of Sir2α to inhibit p53-dependent apoptosis in the cell, thereby decreasing the amount of damage to the cell.

This invention still further provides a method for prolonging the life-span of a cell comprising contacting the cell with an agent that increases the amount of Sir2α in the cell and/or the ability of Sir2α to inhibit p53-dependent apoptosis in the cell, thereby prolonging the life-span of the cell.

Finally, this invention provides two articles of manufacture. The first article of manufacture comprises a packaging material and an agent contained therein that inhibits the ability of Sir2α to inhibit p53-dependent apoptosis, and a label indicating that the agent is used for treating a subject afflicted with cancer, inhibiting the onset of cancer in a subject, and/or inducing the death of a cell.

The second article of manufacture comprises a packaging material and an agent contained therein that increases the amount of Sir2α in a cell and/or the ability of Sir2α to inhibit p53-dependent apoptosis in a cell, and a label indicating that the agent is used for decreasing the amount of damage to a subject's cells caused by physical stress, prolonging the life-span of a subject, decreasing the amount of damage to a cell caused by physical stress, and/or prolonging the life-span of a cell.

DETAILED DESCRIPTION OF THE INVENTION

Definitions

Figure 1A:
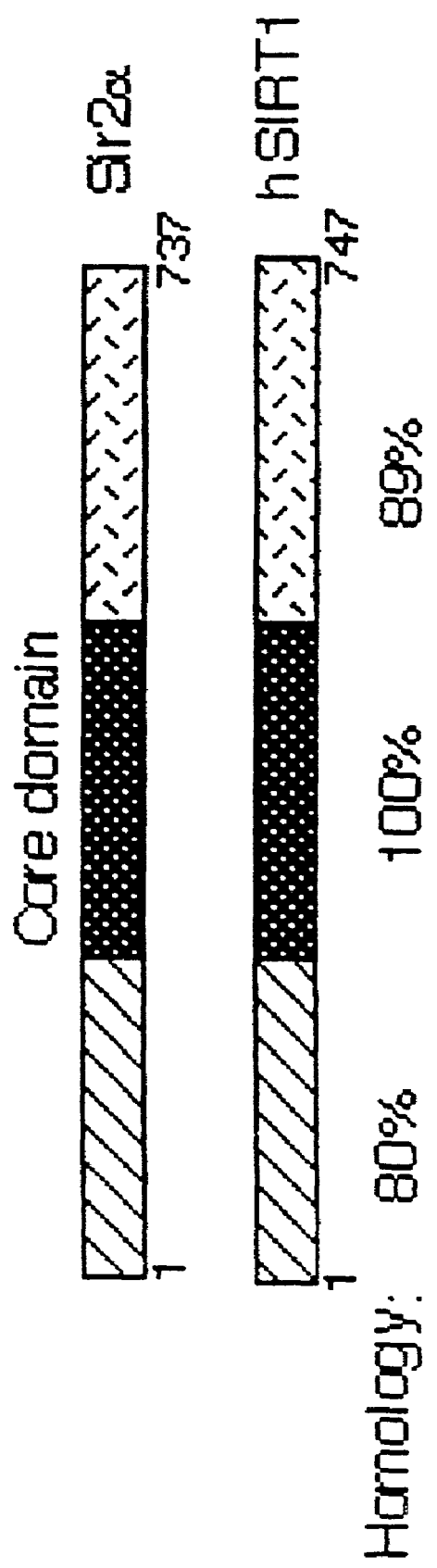
FIG. 1. Interactions between p53 and mammalian Sir2α both in vitro and in vivo. (A) Schematic representation of the high homology regions between mouse Sir2α and human SIRT1 (hSIRT1). The core domain represents the very conserved enzymatic domain among all Sir2 family proteins (Frye, 1999, 2000). (B) The interaction between p53 and hSIRT1 in H460 cells. (C) The interaction between p53 and Sir2α in F9 cells. (D) The interaction between p53 and hSIRT1 in HCT116 cells either at the normal condition (lanes, 1–3) or after DNA damage treatment by etoposide (lanes, 4–6). Western blot analyses of the indicated whole cell extract (WCE) (lanes 1, 4), or immunoprecipitates with anti-Sir2α antibody (IP/anti-Sir2α) (lanes 2, 5) prepared from different cell extracts, or control immunoprecipitates with pre-immunoserum from the same extracts (lanes 3, 6), with anti-p53 monoclonal antibodies (DO-1 for human p53, 421 for mouse p53), or anti-sir2α antibody. (E) Direct interactions of Sir2α with GST-p53. The GST-p53 full length protein (GST-p53) (lane 1), the N-terminus of p53 protein (1–73) (lane 2), the middle part of p53 (100–290) (lane 3), the C-terminus of p53 (290–393) (lane 4), and GST alone (lane 6) were used in GST pull-down assay with in vitro translated $^{35}$S-labeled full length mouse Sir2α.

"Anti-sense nucleic acid" shall mean any nucleic acid which, when introduced into a cell, specifically hybridizes to at least a portion of an mRNA in the cell encoding a protein ("target protein") whose expression is to be inhibited, and thereby inhibits the target protein's expression.

"Catalytic nucleic acid" shall mean a nucleic acid that specifically recognizes a distinct substrate and catalyzes the chemical modification of this substrate.

"DNAzyme" shall mean a catalytic nucleic acid that is DNA or whose catalytic component is DNA, and which specifically recognizes and cleaves a distinct target nucleic acid sequence, which can be either DNA or RNA. Each DNAzyme has a catalytic component (also referred to as a "catalytic domain") and a target sequence-binding component consisting of two binding domains, one on either side of the catalytic domain.

"Inhibiting" the onset of a disorder shall mean either lessening the likelihood of the disorder's onset, or preventing the onset of the disorder entirely. In the preferred embodiment, inhibiting the onset of a disorder means preventing its onset entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996–1997, Roche Molecular Systems, Inc., Branchburg, N.J., USA).

"Ribozyme" shall mean a catalytic nucleic acid molecule which is RNA or whose catalytic component is RNA, and which specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

"Subject" shall mean any animal, such as a human, non-human primate, mouse, rat, guinea pig or rabbit.

"Treating" a disorder shall mean slowing, stopping or reversing the disorder's progression. In the preferred embodiment, treating a disorder means reversing the disorder's progression, ideally to the point of eliminating the disorder itself.

Embodiments of the Invention

This invention provides a method for treating a subject afflicted with cancer comprising administering to the subject a therapeutically effective amount of an agent that inhibits the ability of Sir2α to inhibit p53-dependent apoptosis, thereby treating the subject.

This invention also provides a method for inhibiting the onset of cancer in a subject comprising administering to the subject a prophylactically effective amount of an agent that inhibits the ability of Sir2α to inhibit p53-dependent apoptosis, thereby inhibiting the onset of cancer in the subject. Such inhibition can be caused, for example, by altering the behavior of existing Sir2α or by decreasing Sir2α expression (e.g., via anti-Sir2α nucleic acids such as anti-sense and catalytic nucleic acids such as ribozymes and DNAzymes). Sir2α is exemplified by human Sir2α having GenBank accession number AF083106 and the mouse Sir2α having GenBank accession number AF214646.

In the preferred embodiment of these methods, the subject is a human. The agent used in the instant methods can be any agent that inhibits p53 deacylation, such as vitamin $B_3$ or nicotinamide. In a further embodiment, the instant methods further comprise administering to the subject an agent that enhances p53-dependent apoptosis via a mechanism other than Sir2α inhibition, such as Trichostatin A or Etoposide.

This invention further provides a method for inducing the death of a cell comprising contacting the cell with an agent that inhibits the ability of Sir2α to inhibit p53-dependent apoptosis, thereby inducing the death of the cell.

In the preferred embodiment of this method, the cell is a human cell. The agent used in the instant methods can be any agent that inhibits p53 deacylation, such as vitamin $B_3$ or nicotinamide. In a further embodiment, this method further comprises contacting the cell with an agent that enhances p53-dependent apoptosis via a mechanism other than Sir2α inhibition, such as Trichostatin A or Etoposide.

This invention further provides a method for decreasing the amount of damage to a subject's cells caused by physical stress comprising administering to the subject a prophylactically effective amount of an agent that increases the amount of Sir2α in the subject's cells and/or the ability of Sir2α to inhibit p53-dependent apoptosis in the subject's cells, thereby decreasing the amount of damage to the subject's cells.

The damage to the subject's cells can be any type of cellular damage including, for example, DNA damage and membrane damage. Physical stress includes, without limitation, ultraviolet radiation and oxidation. In this method, the agent can be administered prior to, concurrently with or subsequent to the occurrence of the physical stress.

This invention further provides a method for prolonging the life-span of a subject comprising administering to the subject a prophylactically effective amount of an agent that increases the amount of Sir2α in the subject's cells and/or the ability of Sir2α to inhibit p53-dependent apoptosis in the subject's cells, thereby prolonging the subject's life-span.

In the preferred embodiment of the instant methods, the subject is human. The agent that increases the amount of Sir2α and/or the ability of Sir2α to inhibit p53-dependent apoptosis can be, for example, a Sir2α-encoding nucleic acid.

This invention further provides a method for decreasing the amount of damage to a cell caused by physical stress comprising contacting the cell with an agent that increases the amount of Sir2α in the cell and/or the ability of Sir2α to inhibit p53-dependent apoptosis in the cell, thereby decreasing the amount of damage to the cell.

The damage to the cell can be any type of cellular damage including, for example, DNA damage and membrane damage. Physical stress includes, without limitation, ultraviolet radiation and oxidation. In this method, the agent can be contacted with the cell prior to, concurrently with or subsequent to the occurrence of the physical stress.

This invention still further provides a method for prolonging the life-span of a cell comprising contacting the cell with an agent that increases the amount of Sir2α in the cell and/or the ability of Sir2α to inhibit p53-dependent apoptosis in the cell, thereby prolonging the life-span of the cell.

In the preferred embodiment of the instant methods, the cell is a human cell. The agent that increases the amount of Sir2α and/or the ability of Sir2α to inhibit p53-dependent apoptosis can be, for example, a Sir2α-encoding nucleic acid.

In this invention, administering agents can be effected or performed using any of the various methods and delivery systems known to those skilled in the art. The administering can be performed, for example, intravenously, orally, nasally, via implant, transmucosally, transdermally, intramuscularly, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol) solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Finally, this invention provides two articles of manufacture. The first article of manufacture comprises a packaging material and an agent contained therein that inhibits the ability of Sir2α to inhibit p53-dependent apoptosis, and a label indicating that the agent is used for treating a subject afflicted with cancer, inhibiting the onset of cancer in a subject, and/or inducing the death of a cell.

The second article of manufacture comprises a packaging material and an agent contained therein that increases the amount of Sir2α in a cell and/or the ability of Sir2α to inhibit p53-dependent apoptosis in a cell, and a label indicating that the agent is used for decreasing the amount of damage to a subject's cells caused by physical stress, prolonging the life-span of a subject, decreasing the amount of damage to a cell caused by physical stress, and/or prolonging the life-span of a cell.

This invention is illustrated in the Experimental Details section that follows. This section is set forth to aid in an understanding of the invention but is not intended to, and should not be construed to, limit in any way the invention as set forth in the claims which follow thereafter.

Experimental Details

Introduction

Since homologues of Sir2 have been identified in almost all organisms examined including bacteria, which has no histone proteins (reviewed in Guarente, 2000; Frye, 1999; 2000), it is likely that Sir2 also targets non-histone proteins for functional regulation (Muth et al., 2001). Our preliminary results uncovered a novel activity in protein fractions from mammalian nuclear extract that could effectively deacetylate p53 in the presence of TSA. In support of the notion that mammalian Sir2α targets p53 for functional regulation, we present evidence that mouse Sir2α as well as human SIRT1 can directly bind p53 both in vitro and in vivo, and promotes cell survival under stress by specifically repressing p53-dependent apoptotic response.

Synopsis of Experimental Findings

The NAD-dependent histone deacetylation of Sir2 connects cellular metabolism with gene silencing as well as aging in yeast. Here, we show that mammalian Sir2α physically interacts with p53 and attenuates p53-mediated functions. Nicotinamide (Vitamin B3) inhibits an NAD-dependent p53 deacetylation induced by Sir2α, and also enhances the p53 acetylation levels in vivo. Furthermore, Sir2α represses p53-dependent apoptosis in response to DNA damage and oxidative stress, whereas expression of a Sir2α point-mutant increases the sensitivity of cells in the stress response. Thus, our findings implicate a novel p53 regulatory pathway mediated by mammalian Sir2α. These results have significant implications regarding an important role for Sir2α in modulating the sensitivity of cells in p53-dependent apoptotic response and the possible effect in cancer therapy.

A. Results

Mammalian Sir2α Interacts with p53 Both In Vitro and In Vivo

Figure 1B:
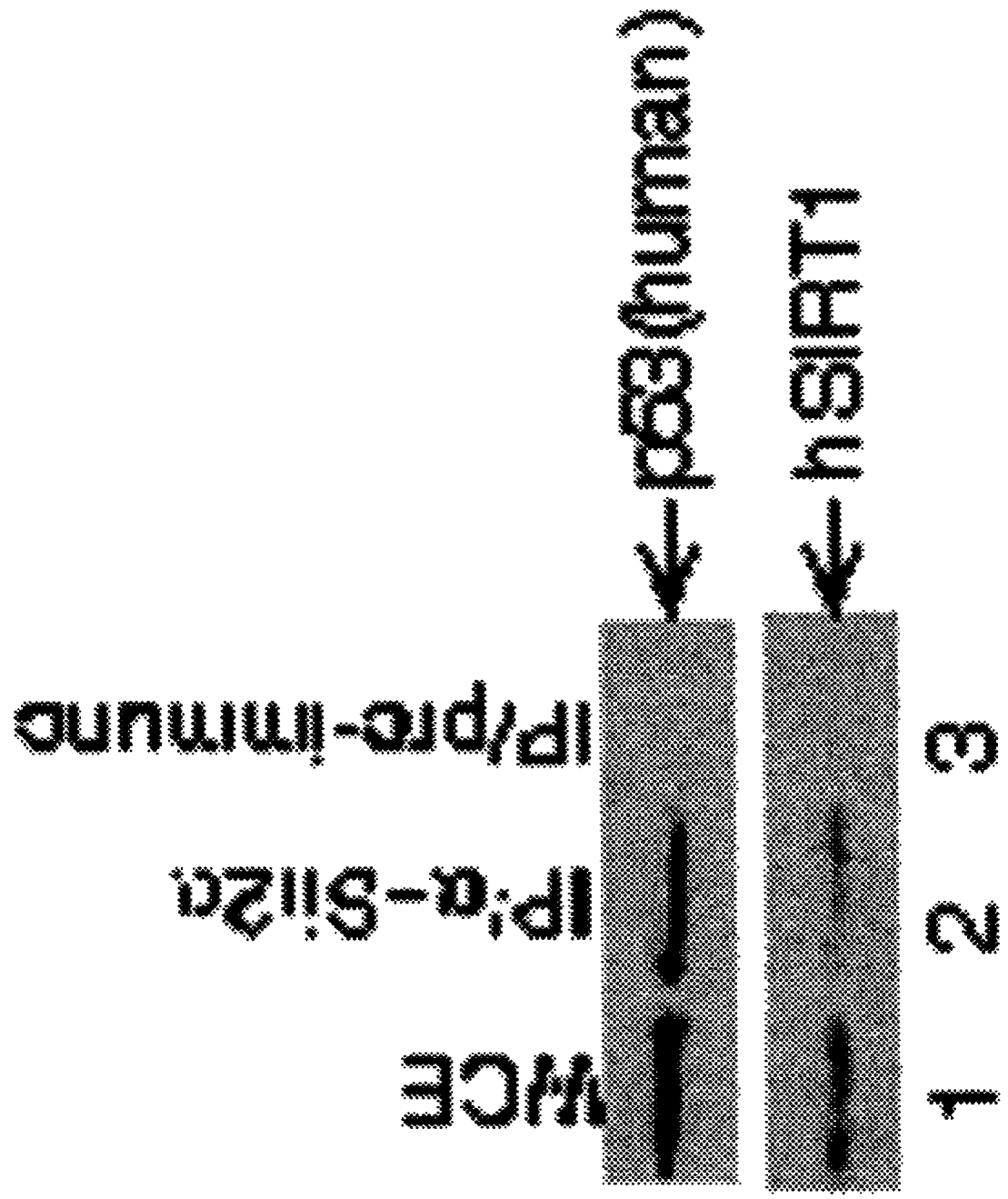
Figure 1C:
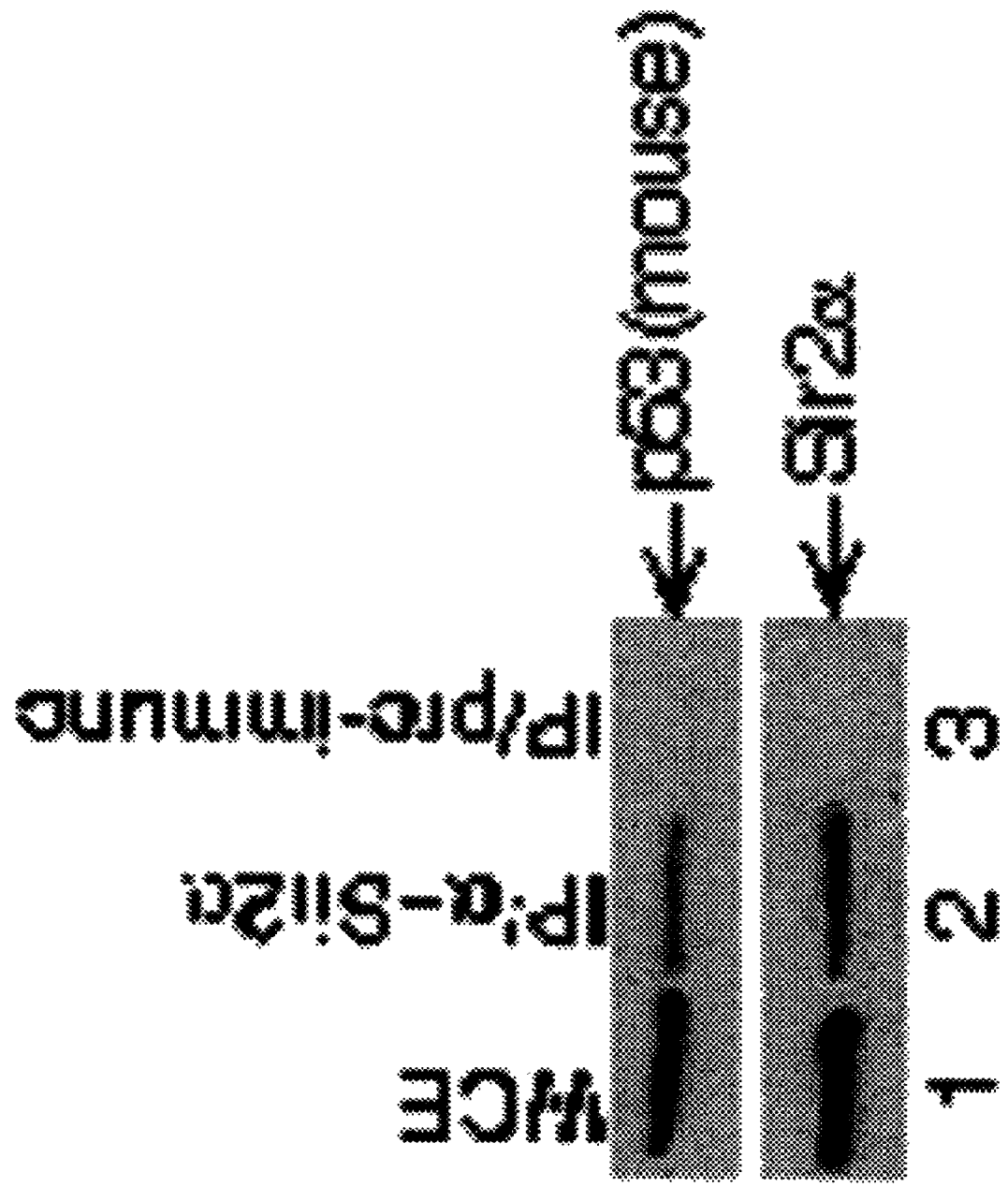
Figure 1D:
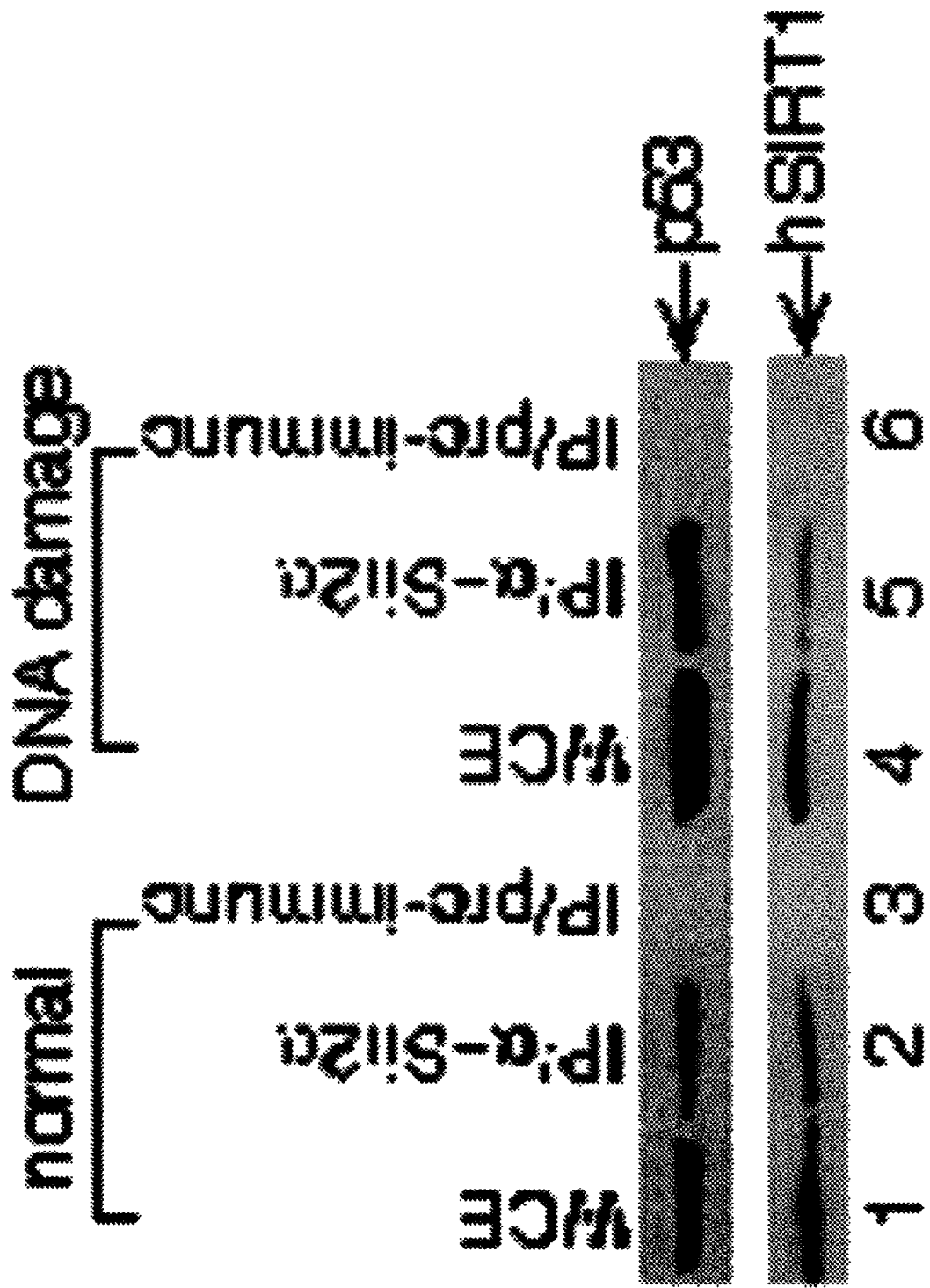

Since mouse Sir2α shares a highly conserved region at the C-terminus with human SIRT1 (FIG. 1A), but not with any other mammalian Sir2 homologs (Frye, 1999; 2000), we developed a polyclonal antibody against the C-terminus (amino acid 480–737) of mouse Sir2α. By western blot analysis, this antibody can detect both mouse Sir2α and human SIRT1 proteins, but not other human Sir2 homologs (see FIGS. 1B,C). Next, we used this antibody to investigate whether p53 interacts with Sir2α or hSIRT1 in normal cells. Cell extracts from both human (H460) and mouse cells (F9), which express wild-type p53 proteins, were immunoprecipitated with α-Sir2α, or with the pre-immune serum. Western blot analysis revealed that this antibody immunoprecipitated both Sir2α and hSIRT1 (lower panels, FIGS. 1B, 1C). More importantly, both human and mouse p53 were clearly detected in the respective α-Sir2α immunoprecipitations from cell extracts, but not in the control immunoprecipitations with the preimmune serum, indicating that p53 interacts with mammalian Sir2α in normal cells. Interestingly, this interaction was strongly detected in the cells after DNA damage treatment (FIG. 1D), suggesting that the possible regulation of p53 by mammalian Sir2α may be still effective after DNA-damage.

Figure 1E:
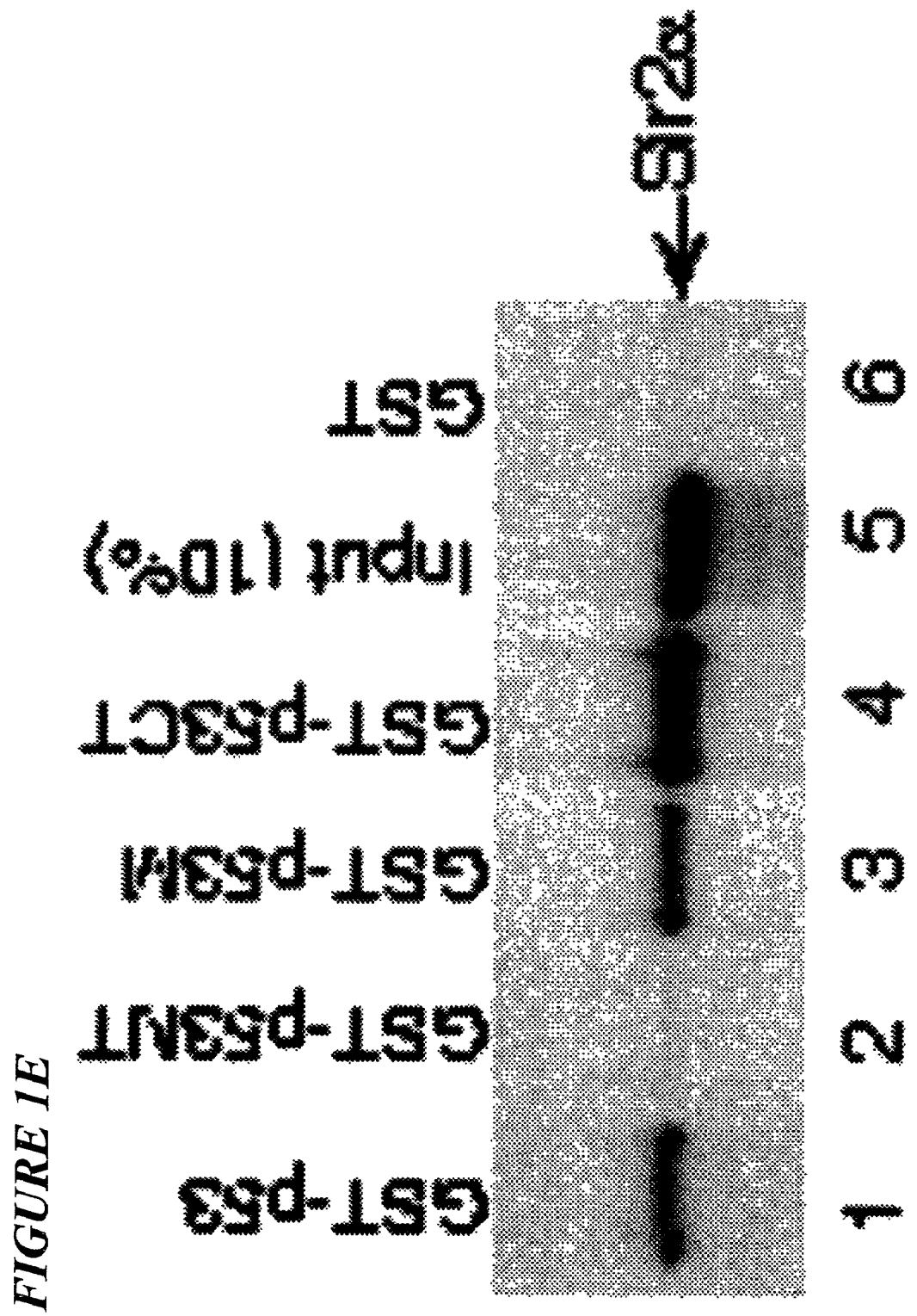

Furthermore, we tested whether Sir2α directly interacts with p53 in vitro. As shown in FIG. 1E, $^{35}$S-labeled in vitro translated Sir2α strongly bound to immobilized GST-p53 but not to immobilized GST alone (lane 1 vs 6). Moreover, Sir2α tightly bound to the C-terminal domain of p53 (GSTp-53CT) (lane 4, FIG. 1E), also bound to the central DNA-binding domain (GST-p53M), but showed no binding to the N-terminal domain of p53 (GST-p53NT) (lane 3 vs 2, FIG. 1E). Thus, the above findings demonstrate that p53 interacts with mammalian Sir2α both in vitro and in vivo.

Deacetylation of p53 by Mammalian Sir2α

Figure 2A:
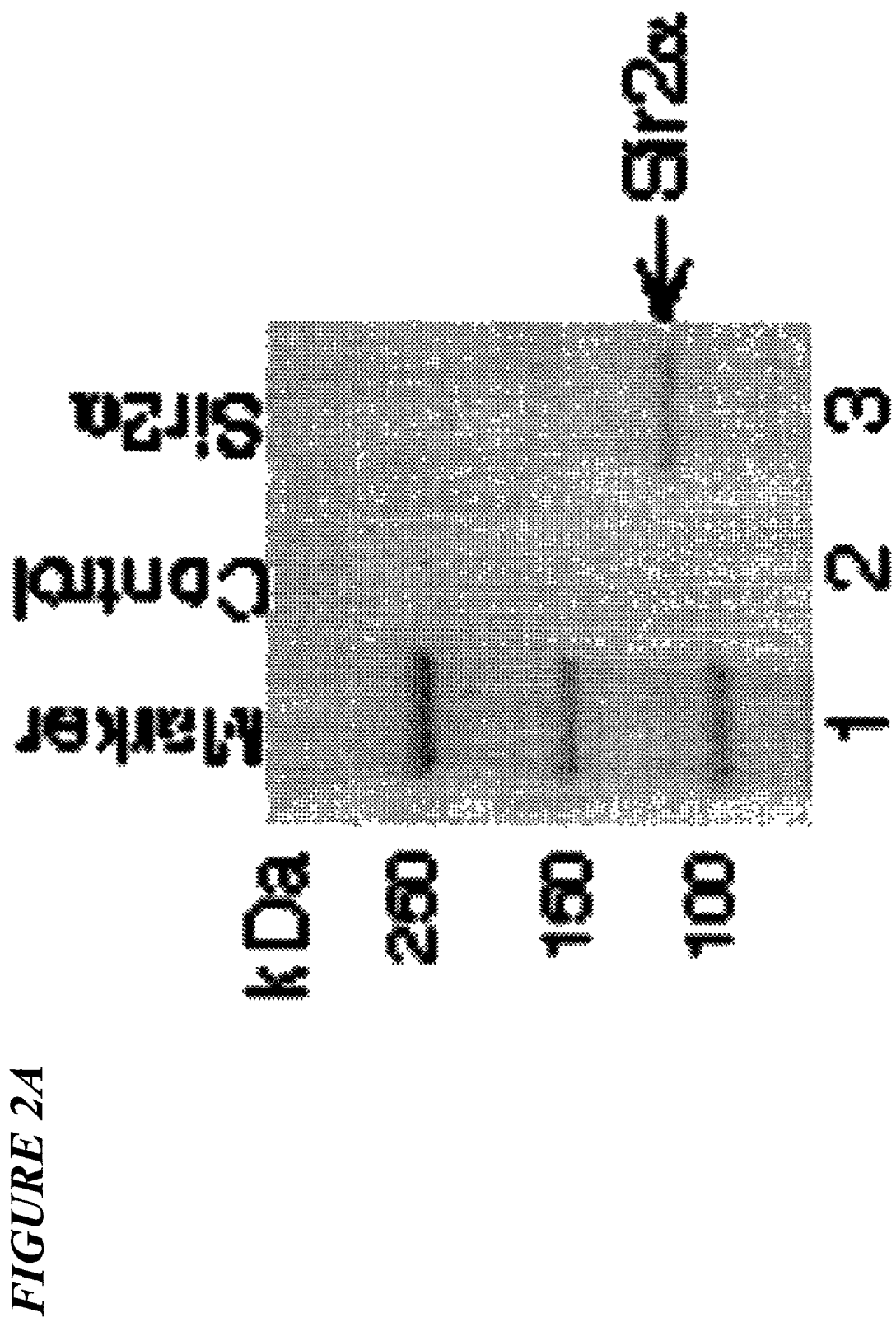
FIG. 2. TSA-insensitive deacetylation of p53 by mammalian Sir2α. (A) Colloidal blue staining of a SDS-PAGE gel containing protein Marker (lane 1), a control eluate from M2 loaded with untransfected cell extract (lane 2), and 100 ng of the highly purified Flag-tagged Sir2α recombinant protein (lane 3). (B) Deacetylation of p53 by Sir2α. 2.5 µg of $^{14}$C-labeled acetylated p53 (lane 1) was incubated with either the control eluate (lane 4), the purified 10 ng of Sir2α (lanes 2 and 3), or the same amount of Sir2α in the presence of 500 nM TSA (lane 5) for 60 min at 30° C. NAD (50 µM) was also added in each reaction except lane 2. The proteins were analyzed by resolution on SDS-PAGE and autoradiography (upper) or Coomassie blue staining (lower). (C) Reduction of the steady-state levels of acetylated p53 by both mouse Sir2α and human SIRT1 expression. Western blot analysis of H1299 cell extracts from the cells cotransfected with p53 and p300 (lane 1), or in combination with Sir2α (lane 2), or in combination with hSIRT1 (lane 4), or Sir2α-355A (lane 3), or hSIRT1-363Y (lane 5), or hSIRT5 (lane 6), or PARP (lane 7) by acetylated p53-specific antibody (upper) or DO-1 for total p53 (lower) The highly conserved histidine residue at the core domain was replaced by alanine for mouse Sir2α (a.a. 355) Sir2α-355A), or replaced by tyrosine for human SIRT1 (a.a. 363) (hSIRT1-363Y). (D) Deacetylation of p53 by Sir2α in the presence of TSA. The acetylated p53 levels in the cells cotransfected with p53 and p300 (lanes 1,3), or cotransfected with p53, p300 and Sir2α (lanes 2,4). Cells were either not treated (lanes 1,2) or treated with 500 nM TSA (lanes 3,4).
Figure 2B:
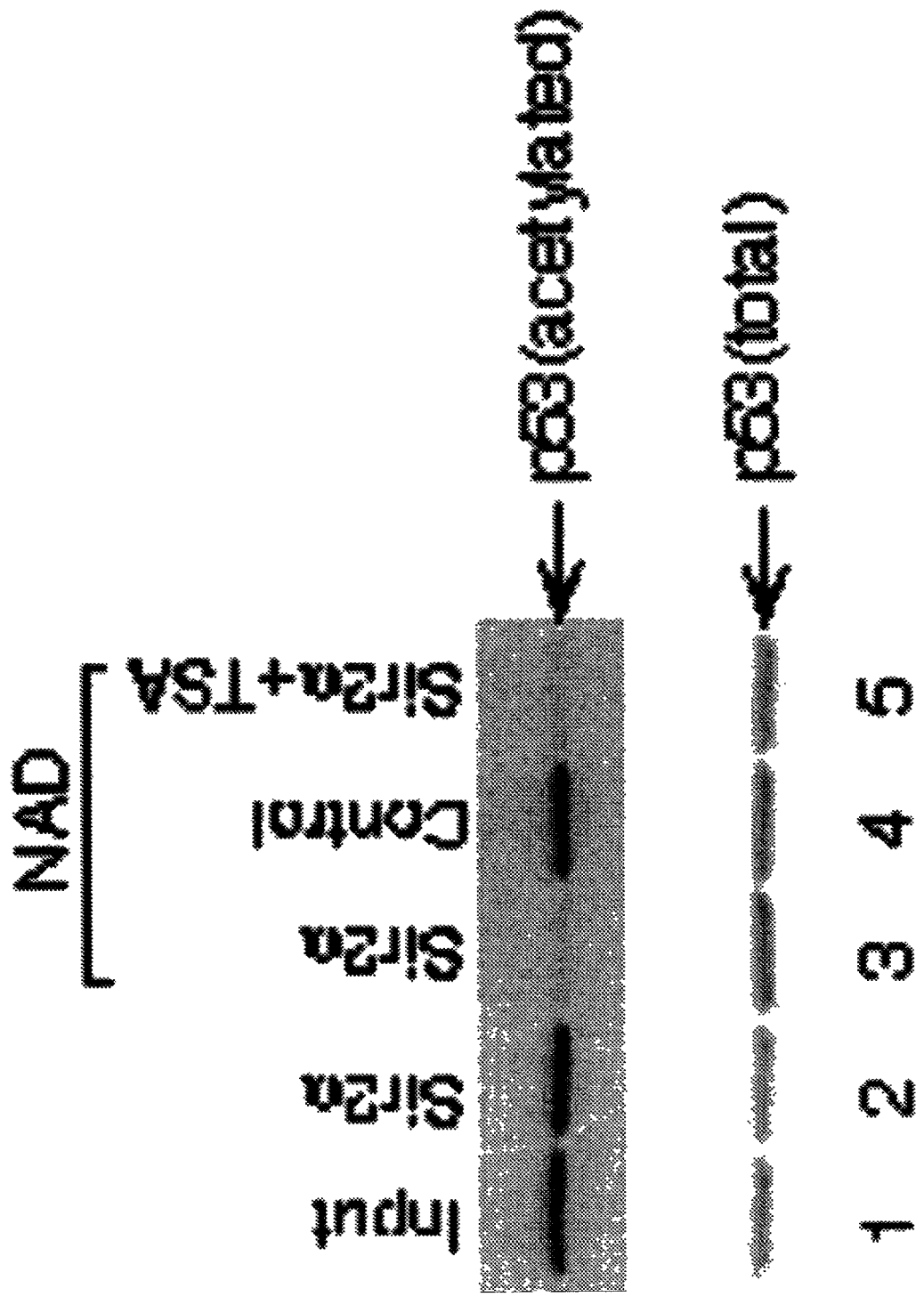

In order to test whether p53 could be specifically deacetylated by mammalian Sir2α in vitro, the mouse Sir2α protein was expressed with the N-terminal Flag epitope in cells and purified to near homogeneity on the M2-agrose affinity column (lane 3, FIG. 2A). As shown in FIG. 2B, $^{14}$C-labeled acetylated p53 was efficiently deacetylated by purified Sir2α (lane 3), but not by a control eluate (lane 4). Importantly, NAD is required for Sir2α-mediated deacetylation of p53 (lane 2 vs. lane 3, FIG. 2B). In addition, the deacetylase inhibitor TSA, which significantly abrogates HDAC1-mediated deacetylase activity on p53 (Luc et al., 2000), had no apparent effect on Sir2α-mediated p53 deacetylation (lane 5, FIG. 2B). These results indicate that the Sir2α can strongly deacetylate p53 in vitro, and that this activity depends on NAD.

Figure 2C:
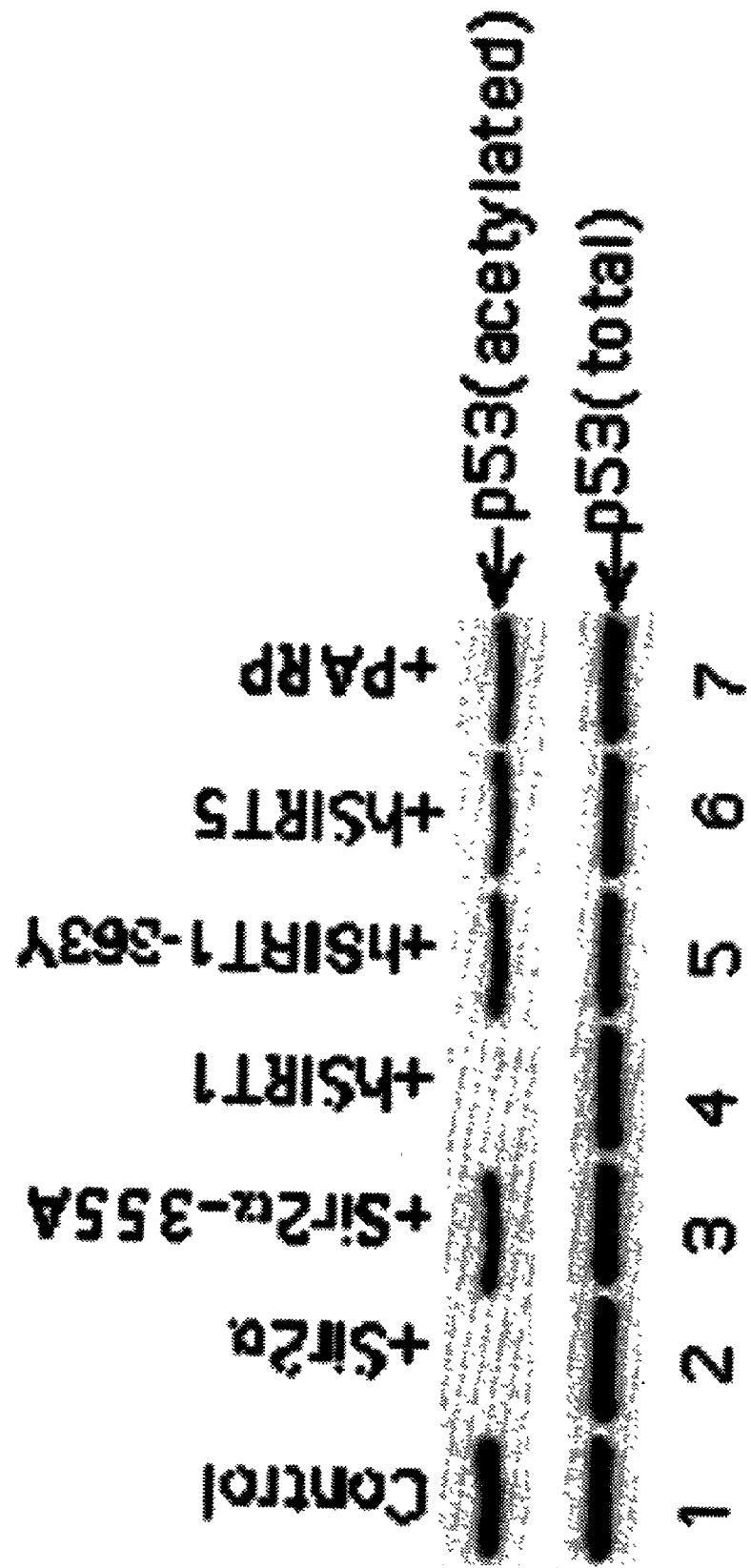
Figure 2D:
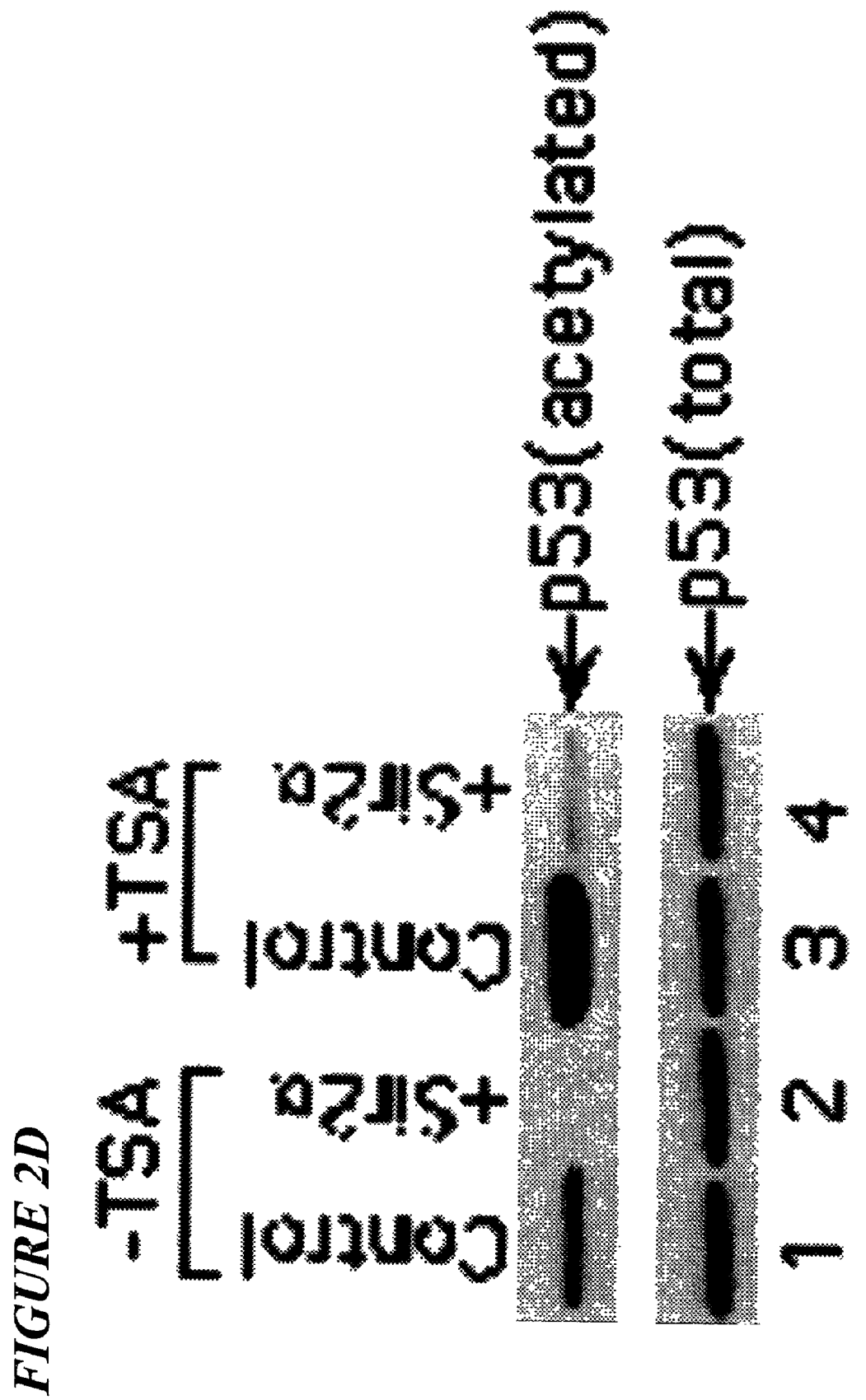

To establish the role for mammalian Sir2α in deacetylating p53 in cells, we used an acetylated p53-specific antibody to monitor the steady-state levels of acetylated p53 in viva (Luo et al., 2000). As indicated in FIG. 2C, a high level of acetylated p53 was found in the cells cotransfected with p300 and p53 (lane 1); however, p53 acetylation levels were significantly abolished by expression of either Sir2α or hSIRT1 (lanes 2, 4). In contrast, a point mutation at the highly conserved histidine residue at the core domain (Sir2α 355A and hSIRT1-363Y) effectively abolished the deacetylase activity (lane 3 vs. 2, lane 5 vs. 4, FIG. 2C). Furthermore, neither SIRT5, another human Sir2 homolog, nor poly(ADP-ribose) polymerase (PARP), whose activity is also NAD-dependent (reviewed in Vaziri et al., 1997), had any significant effect on p53 acetylation (lanes 6,7, FIG. 2C). In addition, in contrast to HDAC-mediated deacetylation of p53 (Luo et al., 2000), Sir2α still strongly deacetylated p53 in the presence of TSA (lane 4 vs 3, FIG. 2D) even though the steady state level of acetylated p53 was elevated when the cells were treated with TSA (lane 3 vs 1, FIG. 2D). Taken together, these data implicate a strong TSA-independent p53 deacetylation activity of mammalian Sir2α.

Inhibition of Sir2α-Mediated p53 Deacetylation by Nicotinamide

To further elucidate the in vivo effect by endogenous Sir2α, we tried to identify an inhibitor for Sir2α-mediated deacetylase activity on p53. Deacetylation of acetyl-lysine by Sir2α is tightly coupled to NAD hydrolysis, producing nicotinamide and a novel acetyl-ADP-ribose compound (1-O-acetyl-ADPribose) (Landry et al., 2000b; Tanner et al., 2000; Tanny and Moazed, 2001). Although the molecular mechanism of Sir2 mediated NAD-dependent deacetylation needs to be detailed, it was proposed that formation of an enzyme-ADP-ribose intermediate through NAD hydrolysis is critical for this chemical reaction (Landry et al., 2000b). Since nicotinamide is the first product from hydrolysis of the pyridinium-N-glycosidic bond of NAD, it may function as an inhibitor for its deacetylase activity (Landry et al., 2000b). We thus tested whether nicotinamide is able to inhibit the deacetylase activity of Sir2α on acetylated p53 in vitro.

Figure 3A:
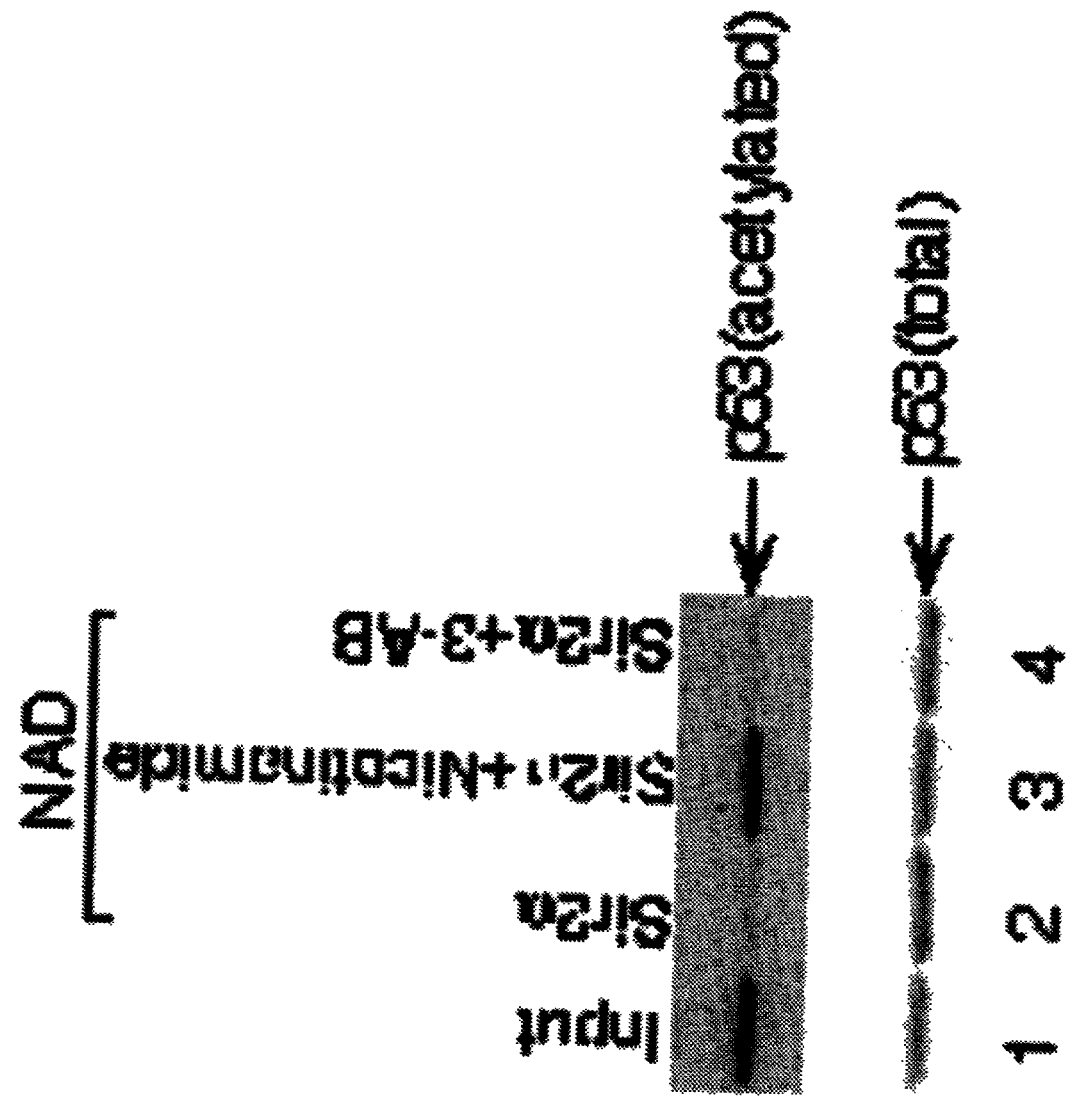
FIG. 3. Abrogation of mammalian Sir2α mediated deacetylation of p53 by nicotinamide. (A) Sir2α-mediated deacetylation of p53 is inhibited by nicotinamide. 2.5 µg of $^{14}$C-labeled acetylated p53 (lane 1) was incubated with 10 ng of purified Sir2α and 50 µM NAD alone (lane 2), or in the presence of either 5 mM of nicotinamide (lane 3) or 3 mM of 3-AB (3-aminobenzamide) (lane 4) for 60 min at 30° C. The proteins were analyzed by resolution on SDS-PAGE and autoradiography (upper) or Coomassie blue staining (lower). (B) Enhancement of endogenous p53 acetylation levels by nicotinamide. Western blot analysis of cell extracts from untreated H460 cells, or the cells treated with etoposide alone (lane 2), or in combination with nicotinamide (lane 3). (C) The Sir2α-mediated deacetylation of endogenous p53 was abrogated in the presence of nicotinamide. Cell extracts from the mock-infected MEF p53(+/+) cells (lanes 1–2, 5–6), or the pBabe-Sir2α infected cells (lanes 3–4, 7–8), either untreated (lanes 1, 3, 5, 7), or treated with etoposide and TSA (lanes 2, 4), or in combination with nicotinamide (lanes 6, 8) for 6 hr were analyzed by western blot with acetylated p53-specific antibody (upper) or DO-1 for total p53 (lower). (D) Synergistic induction of p53 acetylation levels by TSA and nicotinamide during DNA damage response. Western blot analysis of cell extracts from the H460 cells treated with etoposide alone (lane 2), or in combination with TSA (lane 3), or TSA and nicotinamide (lane 4), or TSA and 3-AB (lane 5) for 6 hr by acetylated p53-specific antibody (upper) or DO-1 for total p53 (lower). The cell extracts from untreated cells (lane 1), or treated with ALLN (50 µM) were also included (lane 6).
Figure 3B:
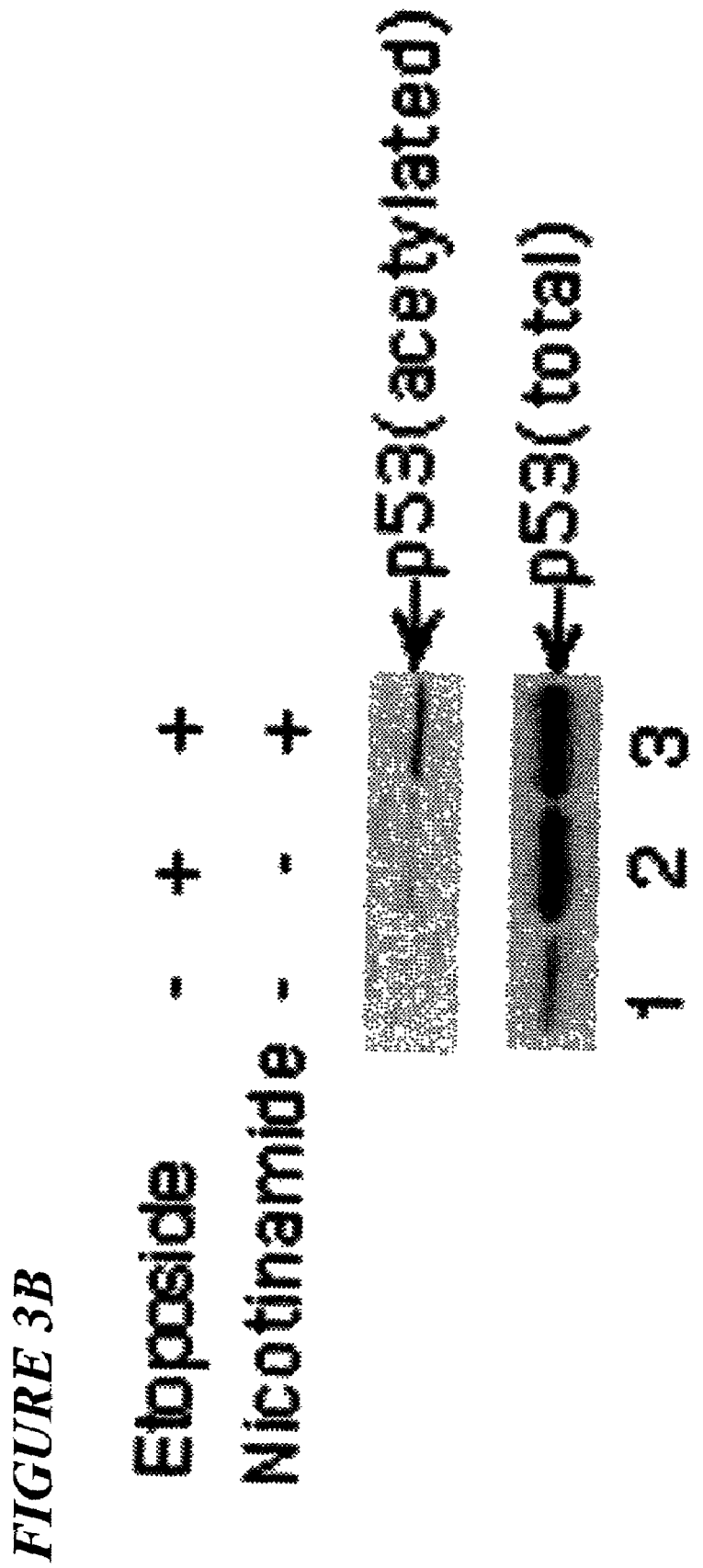

Similar reactions as described above (FIG. 2B), were set up by incubating labeled-p53 substrate, recombinant Sir2α and NAD (50 μM) alone, or in combination with nicotinamide (5 mM). As shown in FIG. 3A. $^{14}$C-labeled acetylated p53 was efficiently deacetylated by Sir2α (lane 2), however, the deacetylation activity was completely inhibited in the presence of nicotinamide (lane 3 vs 2). As a negative control, 3-AB (3-aminobenzamide), a strong inhibitor of PARP which is involved in another type of NAD-dependent protein modifications (Vaziri et al., 1997), showed no significant effect on Sir2α mediated deacetylation (lane 4 vs. 3, FIG. 3A). Significantly, the cellular levels of acetylated p53 induced by DNA damage were enhanced when the cells were treated with nicotinamide (lane 3 vs. 2, FIG. 3B), indicating a potential effect of nicotinamide on endogenous Sir2α-mediated p53 deacetylation.

Figure 3C:
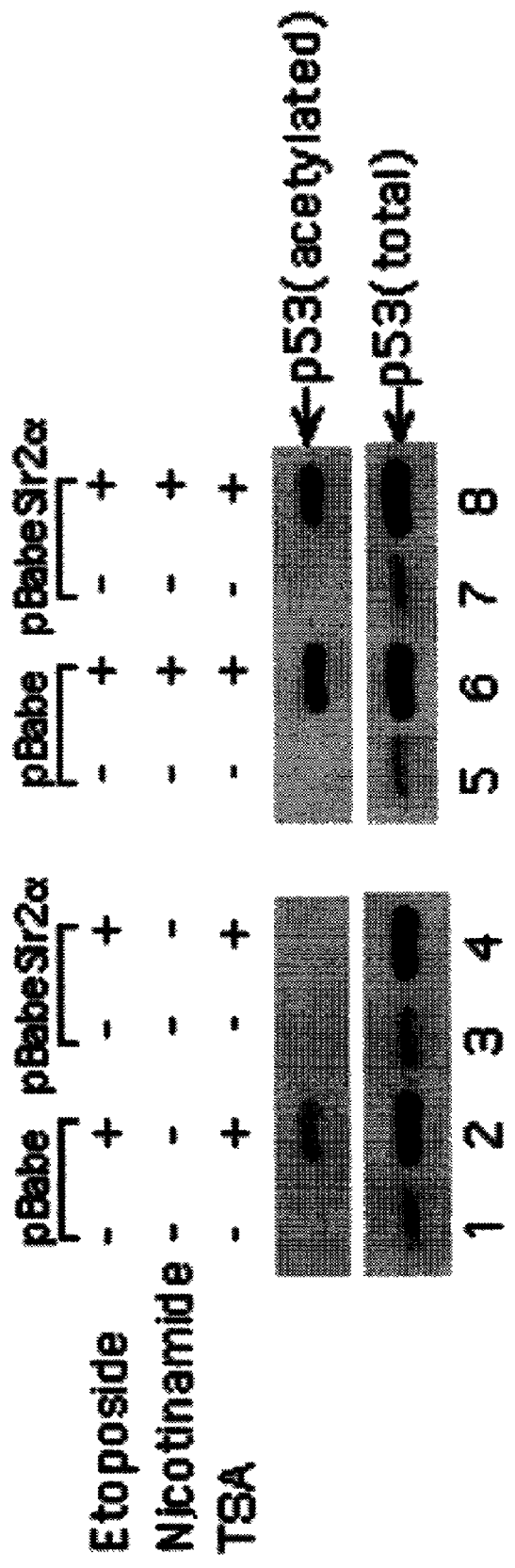

Furthermore, we examined the effect of Sir2α expression on endogenous levels of acetylated p53. Mouse embryonic fibroblast (MEF) cells, which express the wild type of p53, were infected with either a pBabe retrovirus empty vector or a pBabe retrovirus containing Sir2α, and cultured for a week under pharmacological selection. We first examined the protein levels of p53 activation in response to DNA damage in these cells by western blot analysis. Similar protein levels of p53 activation were induced in both types of cells after etoposide treatment for 6 hrs (lanes 3, 4 vs. lanes 1, 2, lower panel, FIG. 3C). In the mock-infected cells, as expected, the acetylation level of p53 was significantly enhanced by DNA damage (lane 2 vs 1, Upper panel, FIG. 3C). However, the same DNA damage treatment failed to stimulate the p53 acetylation in the pBabe-Sir2α infected cells even in the presence of TSA (lane 4 vs 2, Upper panel, FIG. 3C), indicating that Sir2α expression results in deacetylation of endogenous p53. Notably, this Sir2α-mediated effect was completely abrogated by nicotinamide treatment (lane 8 vs 6, FIG. 3C). Thus, these data indicate that Sir2α mediated deacetylation of p53 can be inhibited by nicotinamide both in vitro and in vivo.

Maximum Induction of p53 Acetylation Levels in Normal Cells Requires Inhibition of Endogenous Sir2α Activity After we found that nicotinamide has a strong inhibitory effect on Sir2α mediated deacetylation in vivo (FIG. 3C), we further test whether the endogenous Sir2α is critical in regulating the p53 acetylation levels in normal cells during the DNA damage response.

Figure 3D:
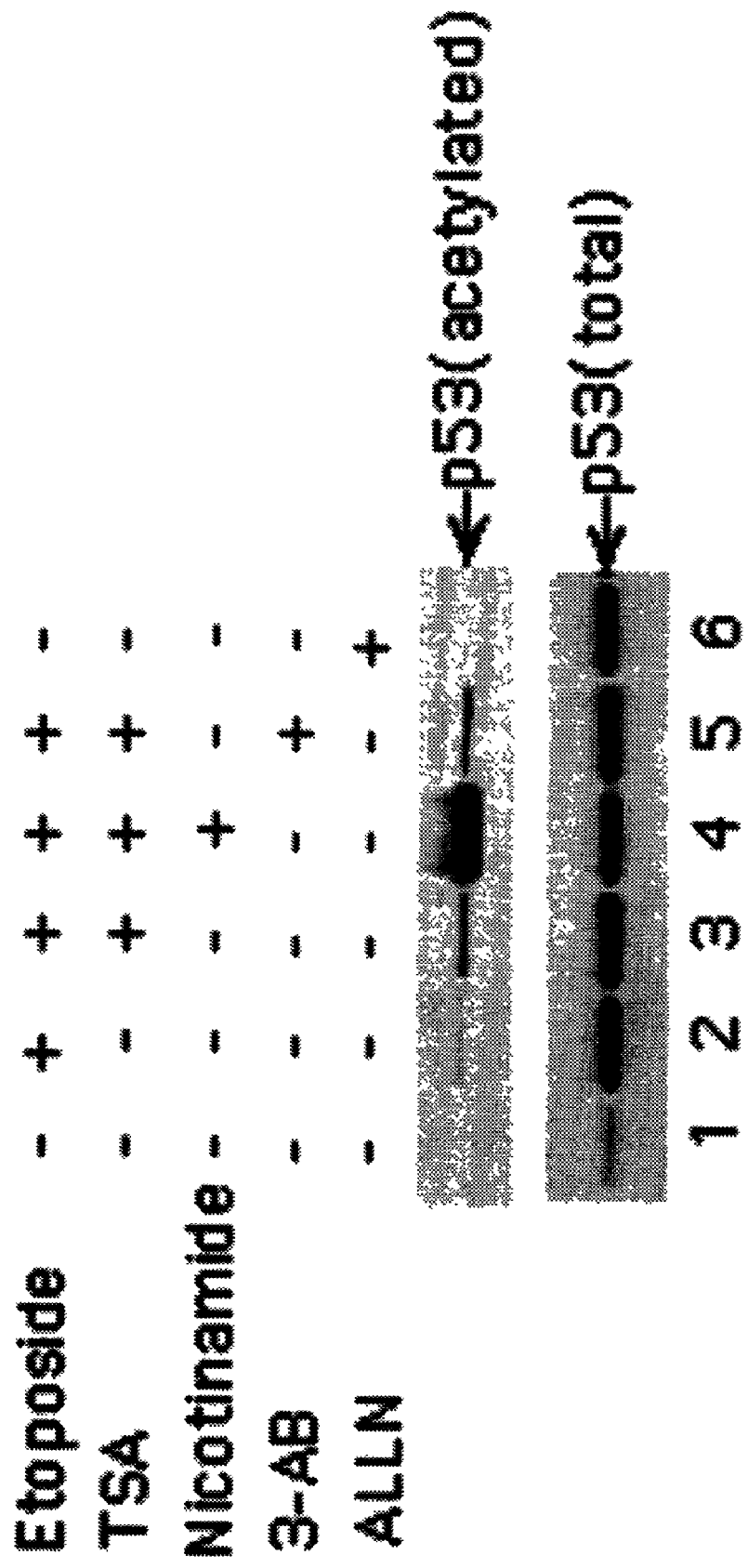

As indicated in FIG. 3D, after the wild-type p53 containing human lung carcinoma cells (H460) were treated by etoposide, acetylation of p53 was indeed induced (lane 2, vs. 1). In contrast, no significant p53 acetylation was detected in the cells treated with a proteasome inhibitor ALLN (Lane 6, FIG. 3D), indicating that the observed stimulation of p53 acetylation is induced by DNA damage, not through p53 stabilization. We have previously shown that p53 can be deacetylated by a PID/MTA2/HDAC1 complex, whose activity is completely abrogated in the presence of TSA (Luo et al., 2000). Therefore, the mild enhancement of the acetylation level of p53 by TSA during DNA damage response may be due mainly to its inhibitory effect on endogenous HDAC1-mediated deacetylase activity (lane 3 vs 2, FIG. 3D). Strikingly, a super induction of p53 acetylation was shown when the cells were treated with both TSA and nicotinamide (lane 4 vs. 3, FIG. 4D). In contrast, 3-AB treatment had no effect on the level of p53 acetylation (lane 5 vs 3, FIG. 3D), indicating that PARP-mediated poly-ADP ribosylation has no effect on p53 acetylation. Similar results were also observed in other cell types including either mouse cells (MEFs, F9) or human cells (BL2, HCT116). Thus, these data clearly indicate that maximum induction of p53 acetylation requires inhibitors for both types of deacetylases (HDAC1 and Sir2α), and that endogenous Sir2α plays an important role in the regulation of the p53 acetylation levels induced by DNA damage.

Figure 4A:
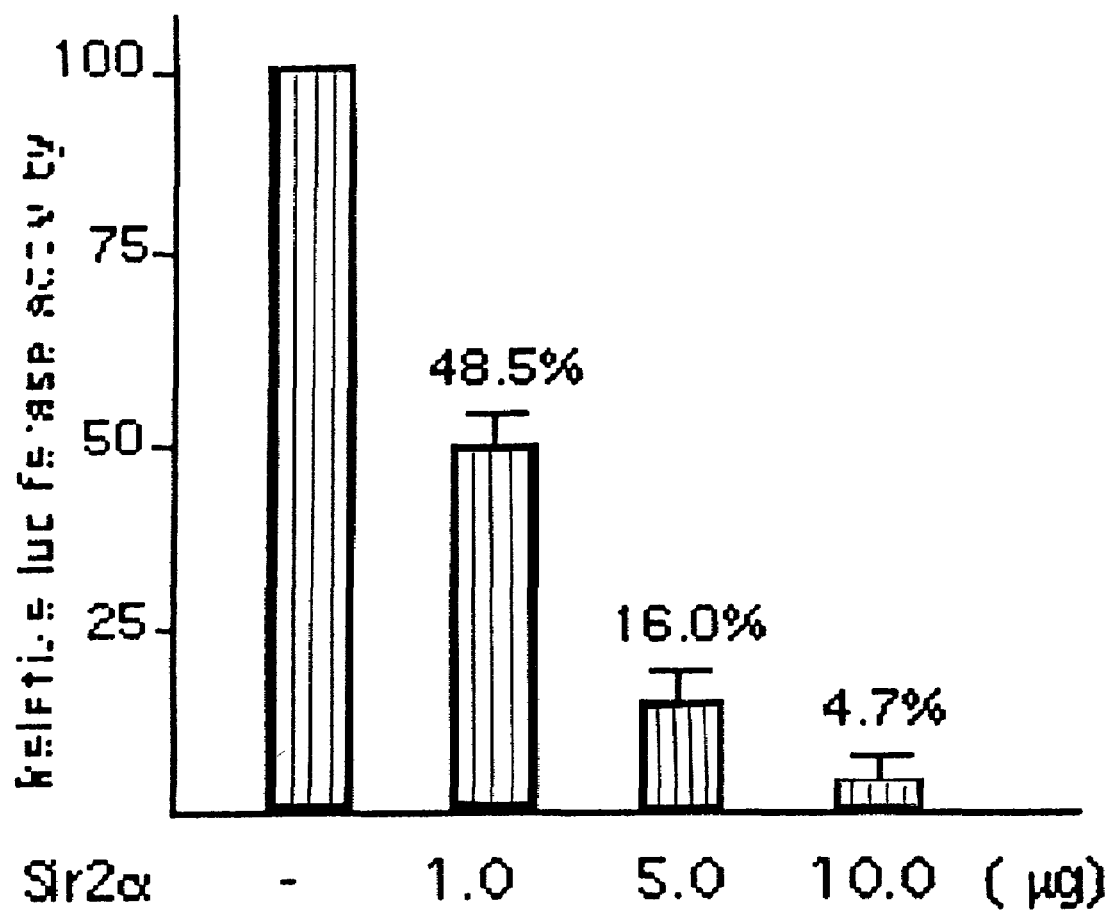
FIG. 4. Repression of p53-mediated transcriptional activation by mammalian Sir2α. (A) MEF (p53−/−) cells were transiently transfected with 10 ng of CMV-p53 alone, or in combination with indicated amount of Sir2α together with the PG13-Luc reporter construct by calcium phosphate precipitation essentially as previously described (Luo et al., 2000). (B) Western blot analysis of indicated transfected H1299 cell extracts with anti-p53 (DO-1), anti-p21 (C-19) and anti-β-actin. (C), (D) MEF (p53−/−) cells were transiently transfected with 10 ng of CMV-p53 alone, or in combination with 5 µg of either CMV-Sir2α, or CMV-hSIRT1, or CMV-hSIRT5 (C), or CMV-Sir2α-355A as indicated (D) together with the PG13-Luc reporter construct. All transfections were done in duplicate and representative experiments depict the average of three experiments with standard deviations indicated.
Figure 4B:
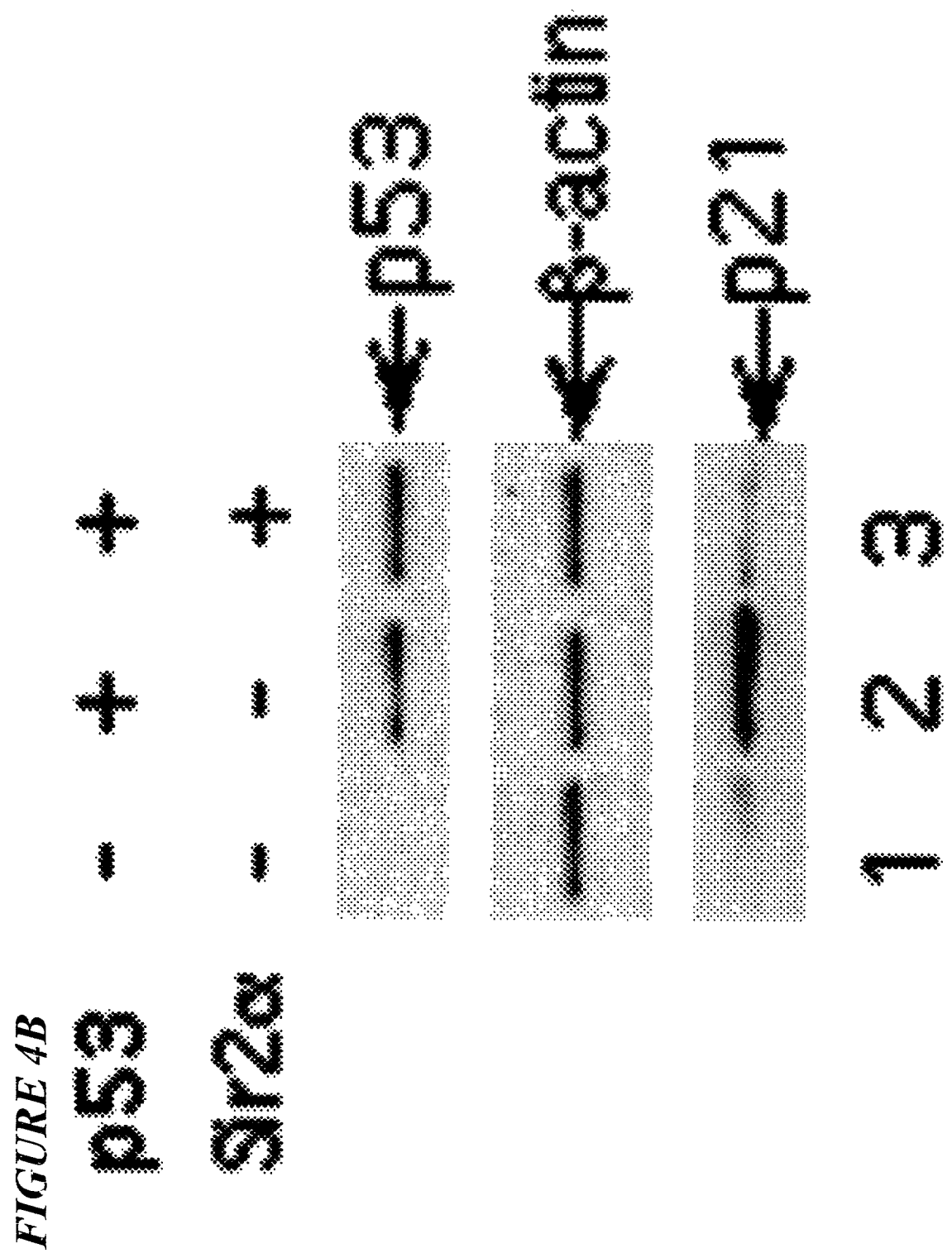
Figure 4C:
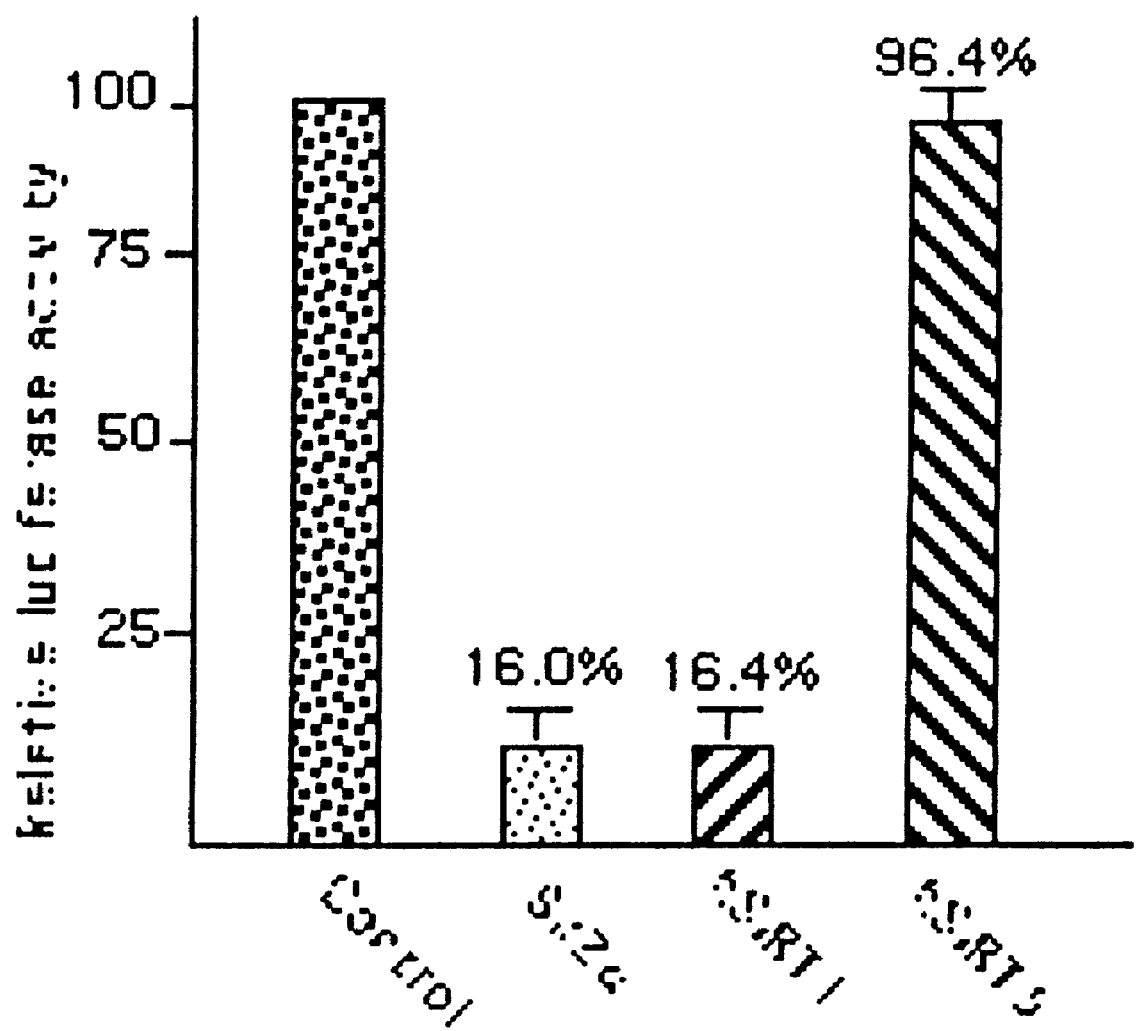
Figure 4D:
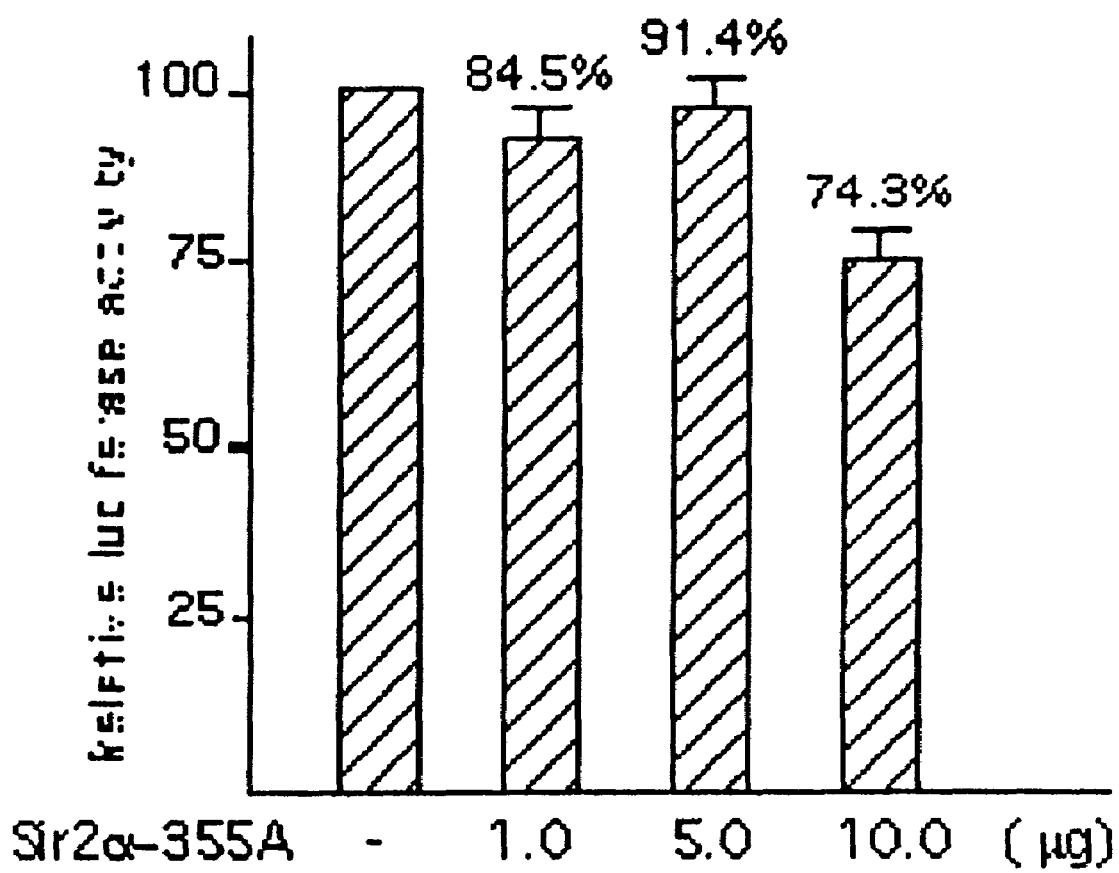

Repression of p53-Mediated Functions by Mammalian Sir2α Requires its Deacetylase Activity To determine the functional consequence of mammalian Sir2α-mediated deacetylation of p53, we tested its effect on p53-mediated transcriptional activation. A mammalian p53 expression vector (CMV-p53), alone or in combination with different amounts of mouse Sir2α expressing vector (CMV-Sir2α) was cotransfected into MEF (p53$^{-/-}$) cells along with a reporter construct containing synthetic p53 binding sites placed upstream of the luciferase gene (PG13-Luc). As shown in FIG. 4A, Sir2α strongly repressed p53-mediated transactivation in a dose-dependent manner (up to 21 fold), and expression of human SIRT1 stewed a similar effect on the p53 target promoter (FIG. 4C). Significantly, Sir2α expression also attenuates p53-dependent induction of endogenous p21 expression (lane 3 vs 2, FIG. 4B). Neither the Sir2α-355A mutant nor SIRT5, both of which are defective in p53 deacetylation (FIG. 2C), had any effect on the p53-mediated transactivation (FIG. 4C, D). These data suggest that mammalian Sir2α specifically represses p53-dependent transactivation, and that this repression requires its deacetylase activity.

Figure 5A:
FIG. 5. Inhibition of p53-dependent apoptosis by Sir2α. (A), (B) H1299 cells were transfected with p53 alone, or cotransfected with p53 and Sir2α, or cotransfected with p53 and Sir2α-355A. After transfection, the cells were fixed, stained for p53 by FITC-conjugated α-p53 antibody, analyzed for apoptotic cells (subG1) according to DNA content (PI staining). (C), (D) Mammalian Sir2α has no effect on the Fas mediated apoptosis. Both mock infected cells and pBabe-Sir2α infected MEF p53(−/−) cells were either not treated (1 and 2) or treated with 100 ng/ml Fas antibody in presence of actinomycine D (0.25 μg/ml) (3 and 4). The experiments were repeated more than three times and the results depict the average of three experiments with standard deviations indicated (B), (C).
Figure 5B:
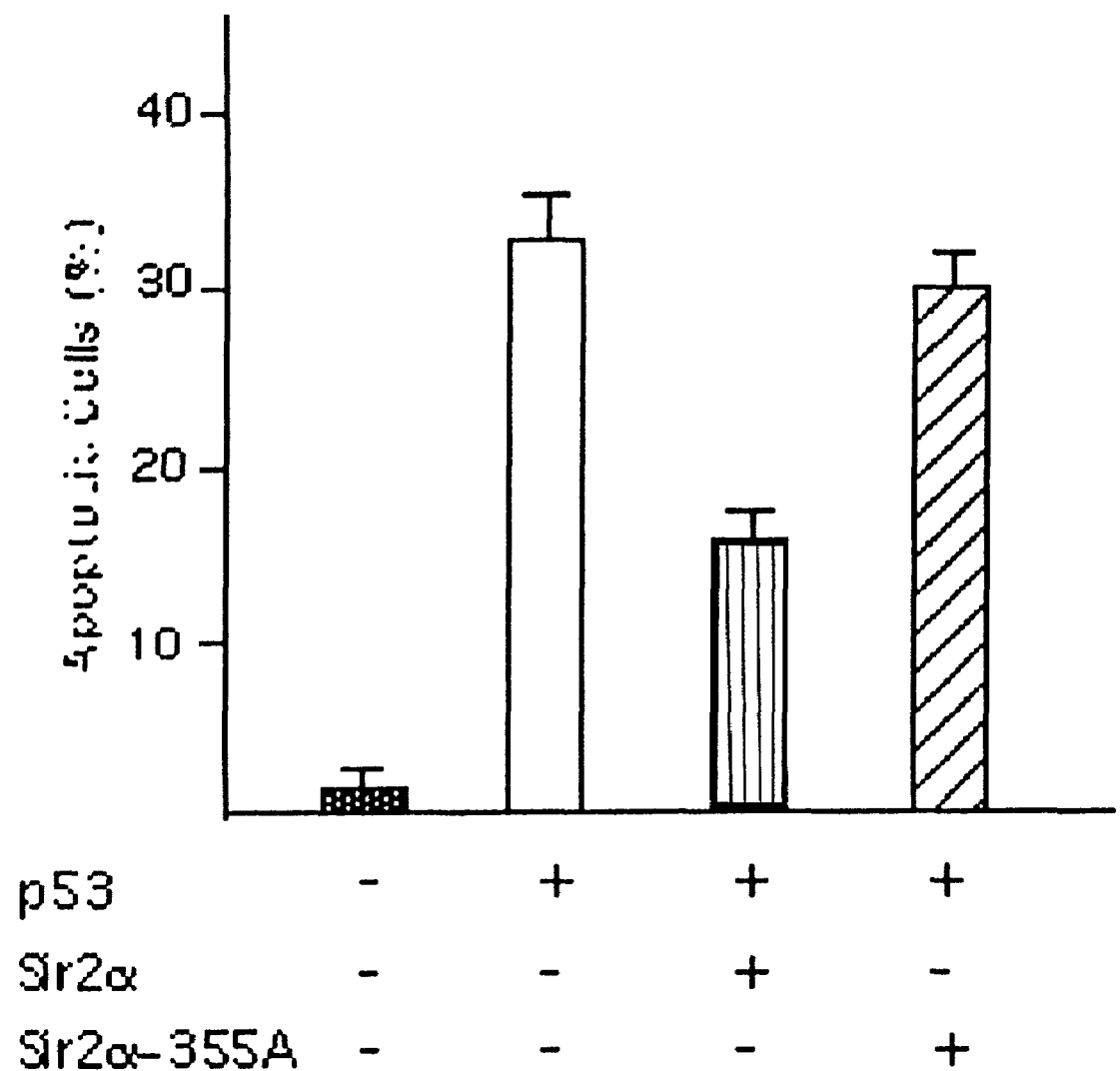

To further test the biological role of mammalian Sir2α, we examined its modulation on p53-dependent apoptosis. p53 null cells (H1299) were transfected with p53 alone or cotransfected with p53 and Sir2α. The transfected cells were fixed, stained for p53, and analyzed for apoptotic cells (SubG1) (Luo et al., 2000). As indicated in FIG. 5A, overexpression of p53 alone induced significant apoptosis (32.3% SubG1). However, co-transfection of p53 with Sir2α significantly reduced the level of apoptosis (16.4% SubG1), while the mutant Sir2α-355A was severely impaired in this effect (29.5% SubG1) (FIGS. 5A, B). Taken together, these data demonstrate that mammalian Sir2α is involved in the regulation of both p53-mediated transcriptional activation and p53-dependent apoptosis, and that the deacetylase activity is required for these Sir2α-mediated effects on p53.

The Role of Mammalian Sir2α in Stress-Induced Apoptotic Response

Figure 6A:
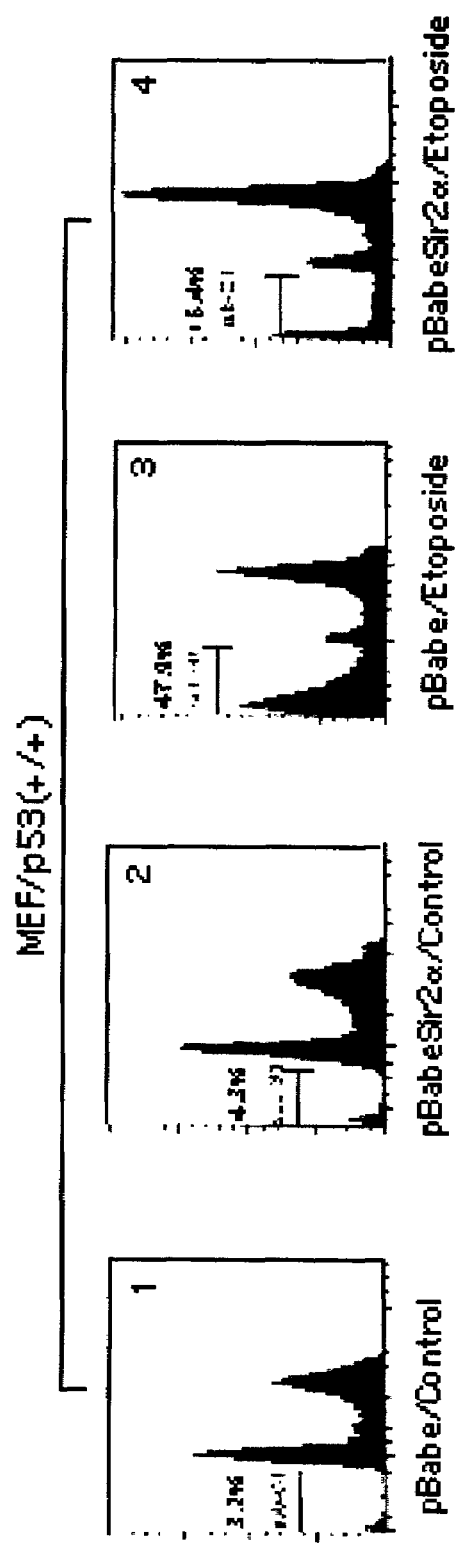
FIG. 6. Inhibition of the p53-dependent apoptosis in response to stress by mammalian Sir2α. (A) Repression of the apoptotic response to DNA damage by Sir2α. Both mock infected cells and pBabe-Sir2α infected MEF p53(+/+) cells were either not treated (1 and 2) or treated with 20 μM etoposide. The cells were analyzed for apoptotic cells (subG1) according to DNA content (PI staining). Similar results were obtained for three times, and the representative data depict the average of three experiments with standard deviations indicated (B). (C) Subcellular localization of p53 and Sir2α in the pBabe-Sir2α infected IMR-90 cells. p53 and Sir2α were detected with either α-p53 (DO-1) (visualized by green fluorescence from secondary antibody staining with anti-mouse IgG-FITC), or affinity purified α-Sir2α antibody (visualized by red fluorescence from secondary antibody staining with anti-rabbit IgG conjugated to Alexa 568). The cells were counterstained with DAPI to visualize the nuclei as essentially described before (Guo et al., 2000). Cells were either not treated (I) or treated with 100 μM $H_2O_2$ (II, III, IV) for 24 hr. (D) Inhibition of the apoptotic response to oxidative stress by mammalian Sir2α. Both mock infected cells and pBabe-Sir2α infected cells were either not treated (I and III) or treated with 200 μM $H_2O_2$ (II and IV). 24 hr later, the cells were photographed under a microscope.
Figure 6B:
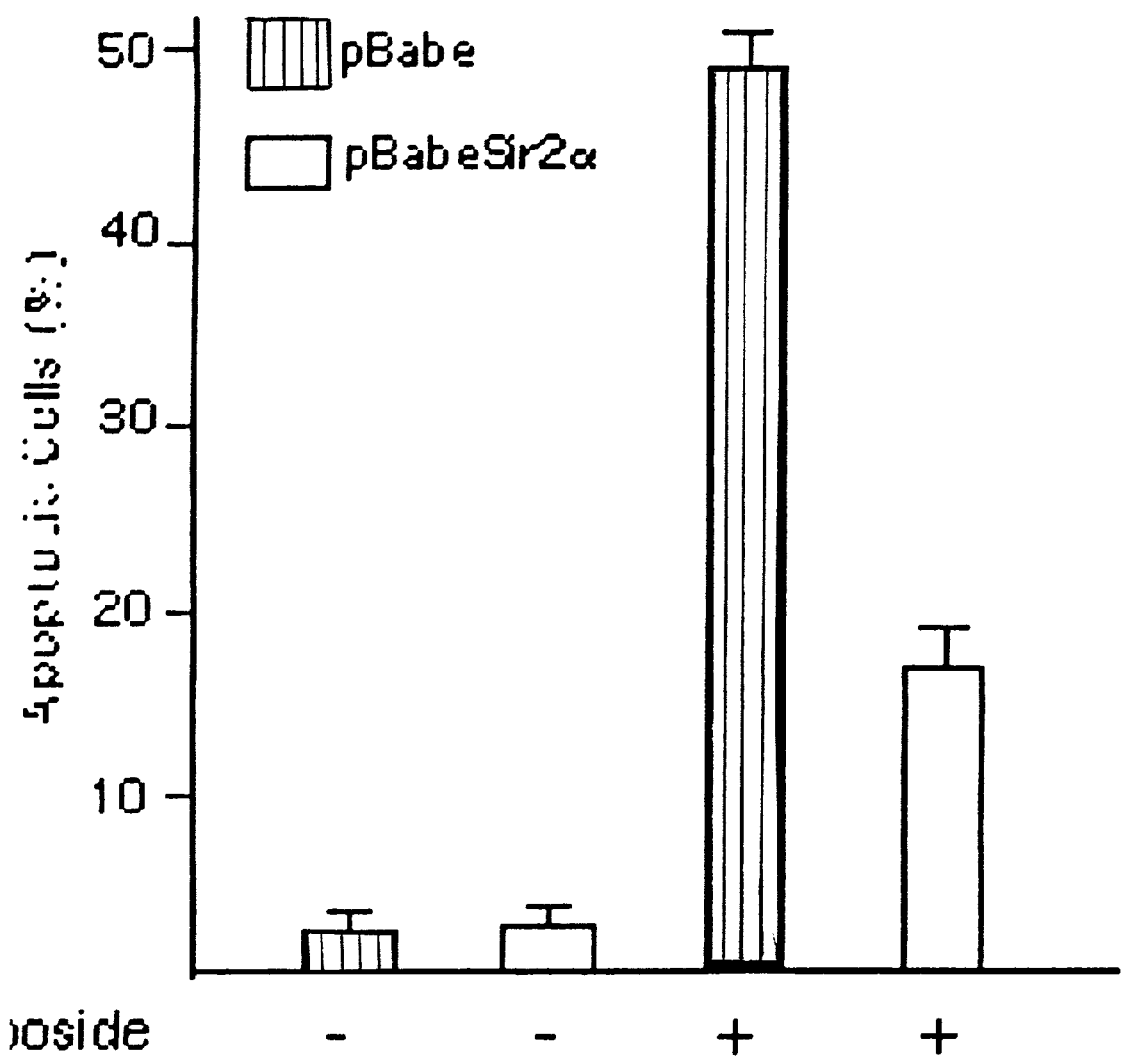

Our data have indicated that mammalian Sir2α can deacetylate p53 both in vitro and in vivo (FIG. 2). More importantly, Sir2α can attenuate p53-mediated transcriptional activation (FIG. 4). To elucidate the physiological significance for this Sir2α-mediated regulation, we examined its effect on DNA damage-induced apoptotic response. For this study, we chose the same MEF (p53$^{+/+}$) cells as described above (FIG. 3C), which were infected with either a pBabe retrovirus empty vector or a pBabe retrovirus containing Sir2α. After the DNA damage treatment by etoposide, the cells were stained with PI and analyzed by flow cytometric analysis for apoptotic cells (SubG1) according to DNA content. As shown in FIG. 6A, the cells mock infected with the pBabe-vector were susceptible to etoposide-induced cell death, with about 48% of the cells apoptotic after exposure to 20 μM of etoposide (3 vs. 1, FIG. 6A). In contrast, the pBabe-Sir2α-infected MEF (p53$^{+/+}$) cells were more resistant to apoptosis induced by the same dose of etoposide, with only 16.4% apoptotic cells (4 vs. 3, FIGS. 6A, B). Since no significant apoptosis was detected in MEF (p53$^{-/-}$) cells by the same treatment, the induced apoptosis observed in MEF (p53$^{+/+}$) cells is totally p53-dependent. Thus, these results indicate that Sir2α significantly inhibits p53-dependent apoptosis in response to DNA damage.

Figure 6C:
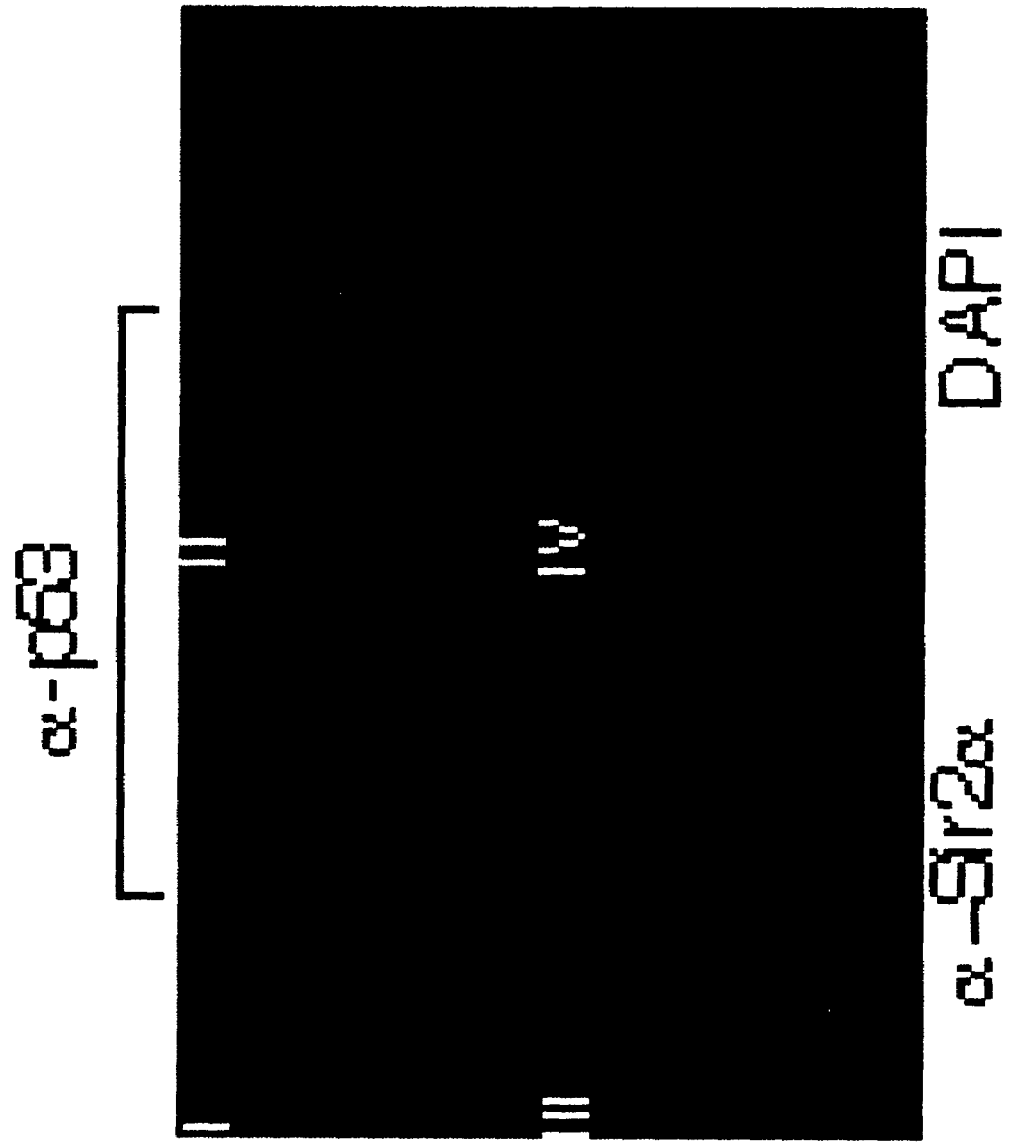
Figure 6D:
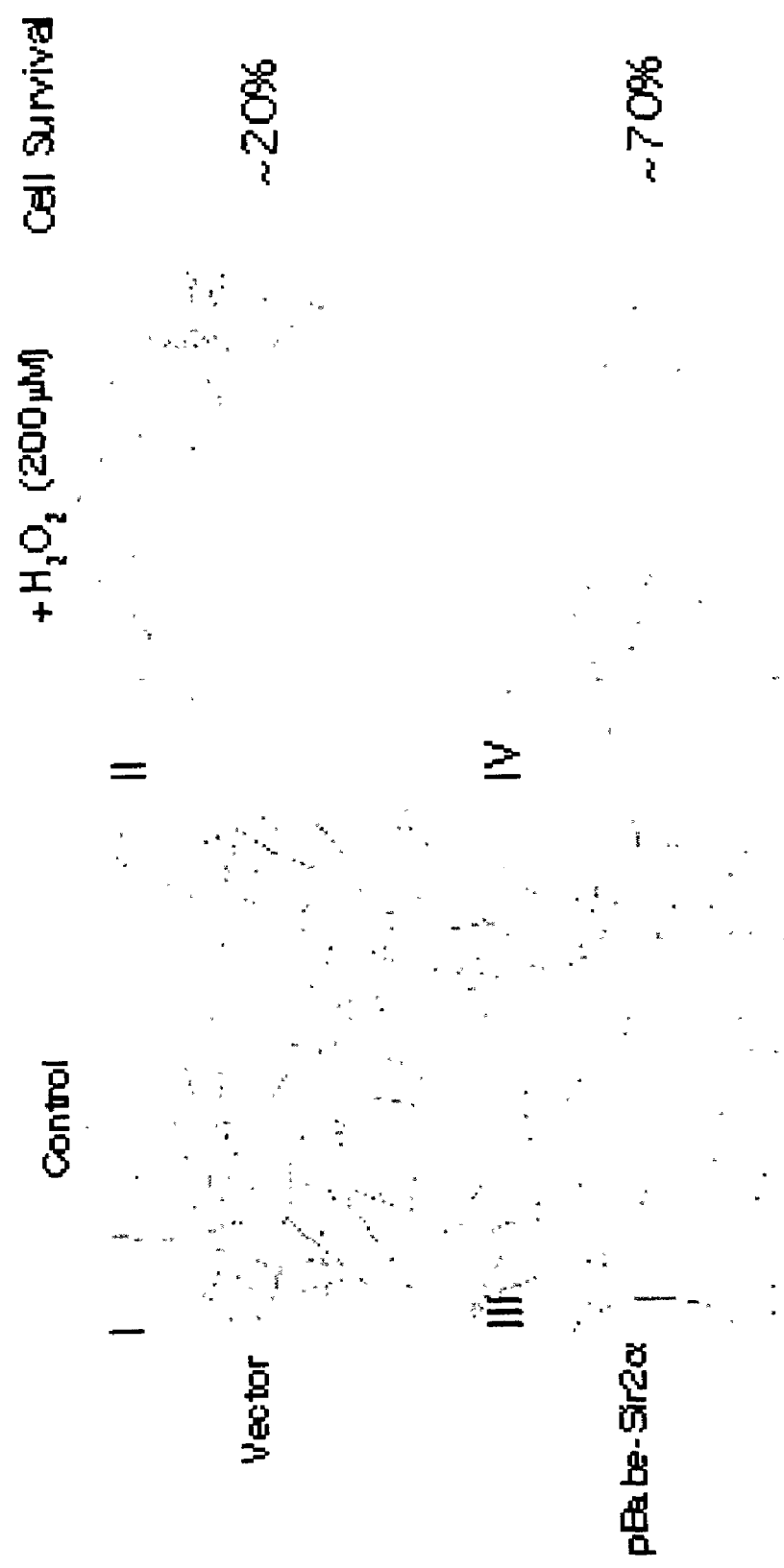

Since stimulation of p53 acetylation as well as p53-dependent apoptosis have also been implicated in many other types of stress response (reviewed in Ito et al., 2001), we examined the role of mammalian Sir2α in the oxidative stress response. Recent studies have indicated that oxidative stress-induced cell death is p53-dependent (Yin et al., 1998; Migliaccio et al., 1999). We chose early-passage normal human fibroblast (NHF) IMR-90 cells for this study since it has been demonstrated that p53-dependent apoptosis can be strongly induced by hydrogen peroxide treatment in these cells (Chen et al., 2000). IMR-90 cells were infected with either a pBabe retrovirus empty vector or a pBabe retrovirus containing Sir2α, and cultured for a week under pharmacological selection. By immunofluorescence staining, we found that p53 in these infected cells was induced significantly after hydrogen peroxide treatment, along with Sir2α localized in the nuclei detected by immunostaining with specific antibodies (FIG. 6C). Importantly, Sir2α expression significantly promotes cell survival under oxidative stress. As indicated in FIG. 6D, the cells mock infected with the pBabe-vector were susceptible to $H_2O_2$-induced cell death, with more than 80% of the cells being killed after 24 hr exposure to 200 μM $H_2O_2$ (II vs. I). In contrast, the pBabe-Sir2α infected cells were much more resistant to death by the same dose of $H_2O_2$, with about 70% of the cells surviving after 24 hr of $H_2O_2$ treatment (IV vs. III, FIG. 6D).

Taken together, these results suggest that mammalian Sir2α promotes cell survival under stress by inhibiting p53-dependent apoptosis.

Mammalian Sir2α has no Effect on p53-Independent Cell Death Induced by Anti-Fas

Figure 5C:
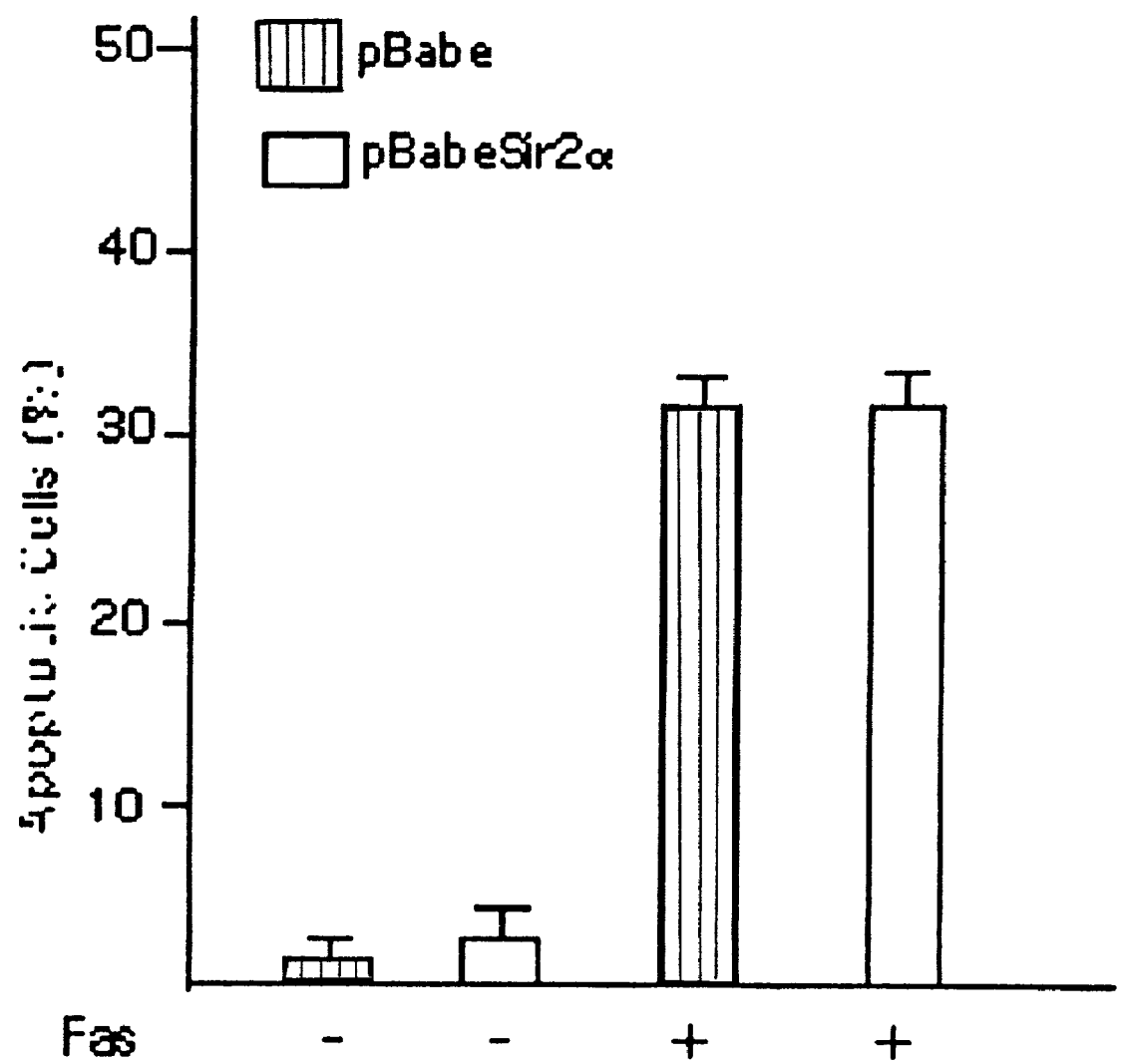
Figure 5D:
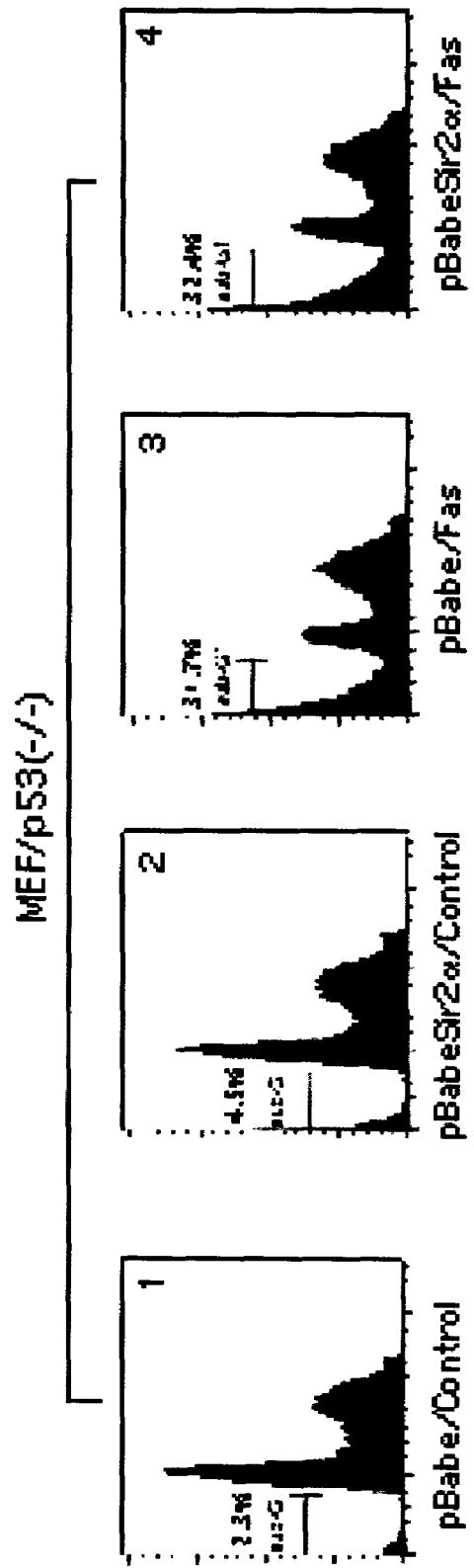

In order to determine the specificity of mammalian Sir2α-mediated protection of cells from apoptosis, we examined whether Sir2α has any effect on p53-independent, Fas-mediated apoptosis. The MEF (p53$^{-/-}$) cells were first infected with either a pBabe retrovirus empty vector or a pBabe retrovirus containing Sir2α, then cultured for a week under pharmacological selection. After the treatment by anti-Fas (100 ng/ml) for 24 hrs, the cells were harvested and further analyzed for apoptotic cells (SubG1). As shown in FIG. 5D, the cells mock infected with the pBabe vector were susceptible to anti-Fas induced cell death, with about 31.7% of the cells becoming apoptotic. However, in contrast to the strong protection of p53-dependent apoptosis by Sir2α during DNA damage response in the MEF (p53$^{+/+}$) cells (FIGS. 6A, B), Sir2α expression had no significant effect on Fas-mediated apoptosis in the MEF (p53$^{-/-}$) cells (FIGS. 5C, D). Thus, these results further support a specific role for mammalian Sir2α in regulating p53-mediated apoptosis.

Figure 7A:
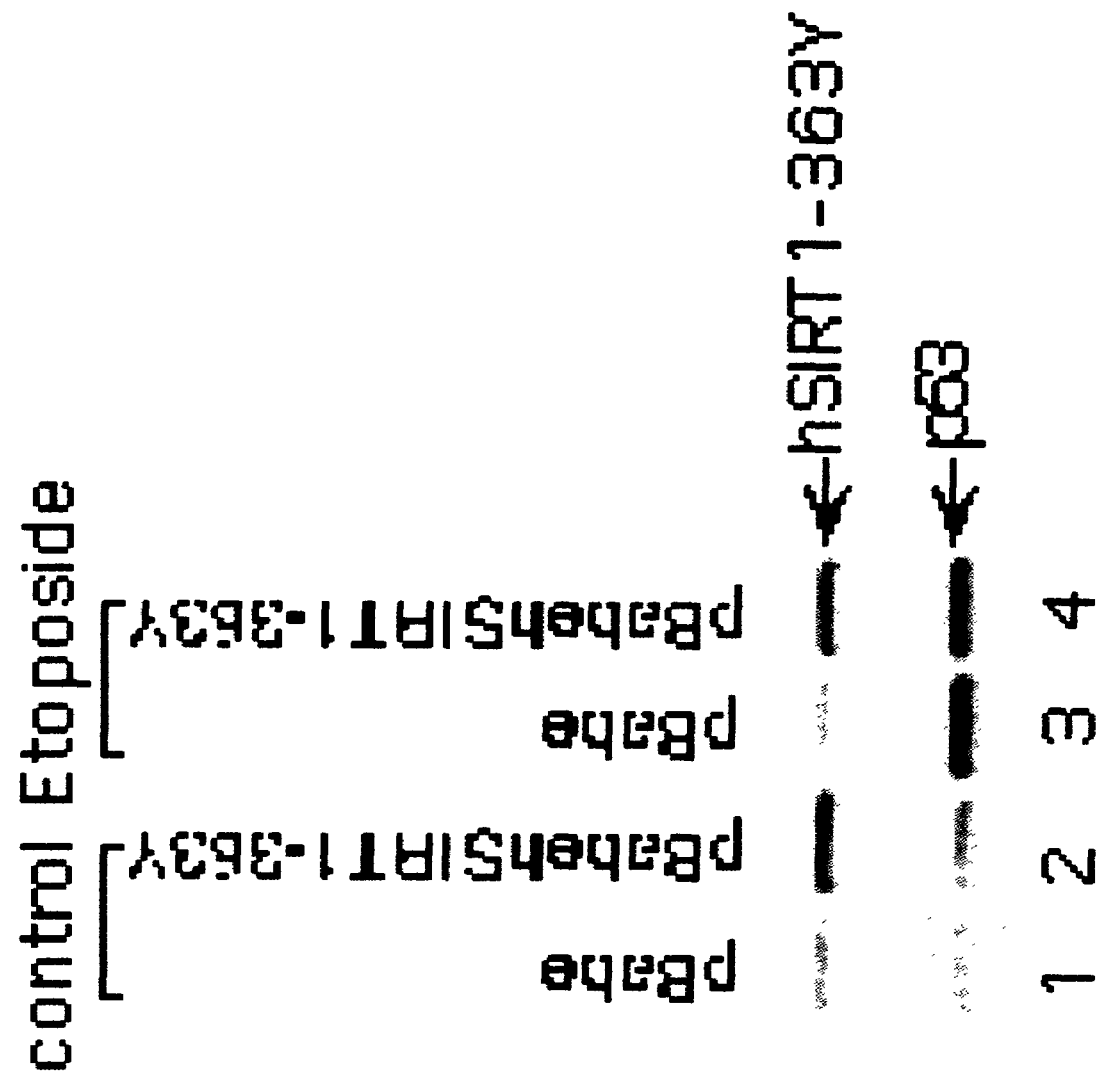
FIG. 7. Expression of a Sir2α point mutant (hSIRT1-363Y) increases the sensitivity of the cells in response to stress. (A) The levels of p53 are induced by DNA damage in both mock infected and pBabe-hSIRT1-363Y infected cells. Western blot analysis of the cell extracts from both types of cells by anti-Sir2 polyclonal antibody (upper) or anti-p53 monoclonal antibody (DO-1) (lower). Cells were either not treated (lanes 1,2) or treated with 20 μM of epotoside (lanes 3,4) for 6 hr. (B) Expression of the Sir2α mutant enhances the acetylated p53 levels induced by DNA damage. The cell extracts obtained from treated or untreated cells were first immunoprecipitated with anti-acetylated p53 antibody and the immunoprecipitates were analyzed by western blot with α-p53 (DO-1). (C) DNA damage induced expression of p21 and Bax in both mock infected and pBabe-hSIRT1-363Y infected cells. Both types of cells were γ-irradiated (3 or 6 Gy), 3 hr later, the cells were collected for western blot analysis for p53, p21, Bax and β-actin. (D), (E) Expression of the Sir2α mutant increases the sensitivity of the cells in stress-induced apoptotic response. Both mock infected cells and pBabe-hSIRT1-363Y infected cells were either not treated (I and III) or treated with 50 μM $H_2O_2$ (II and IV) (E), or treated with different concentrations of adriamycin as indicated. 48 hr later, the cells were collected for analysis (D).
Figure 7B:
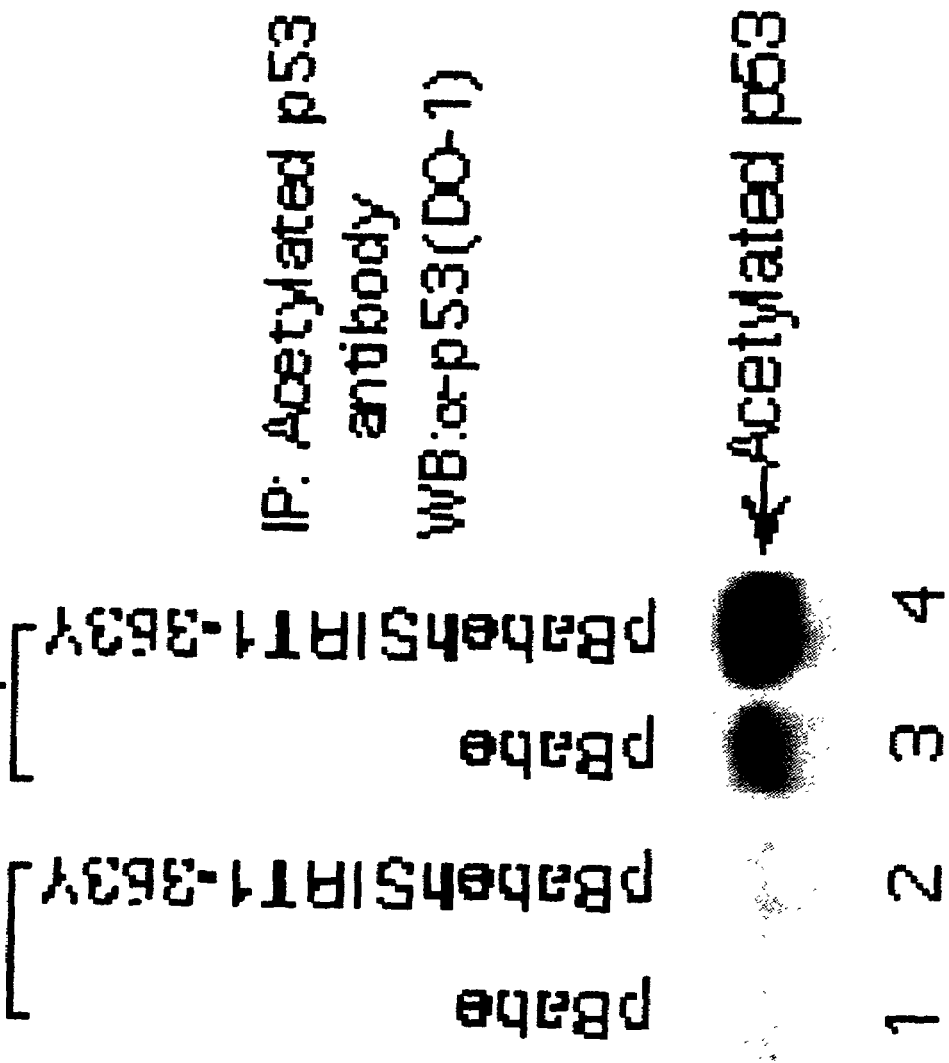
Figure 7C:
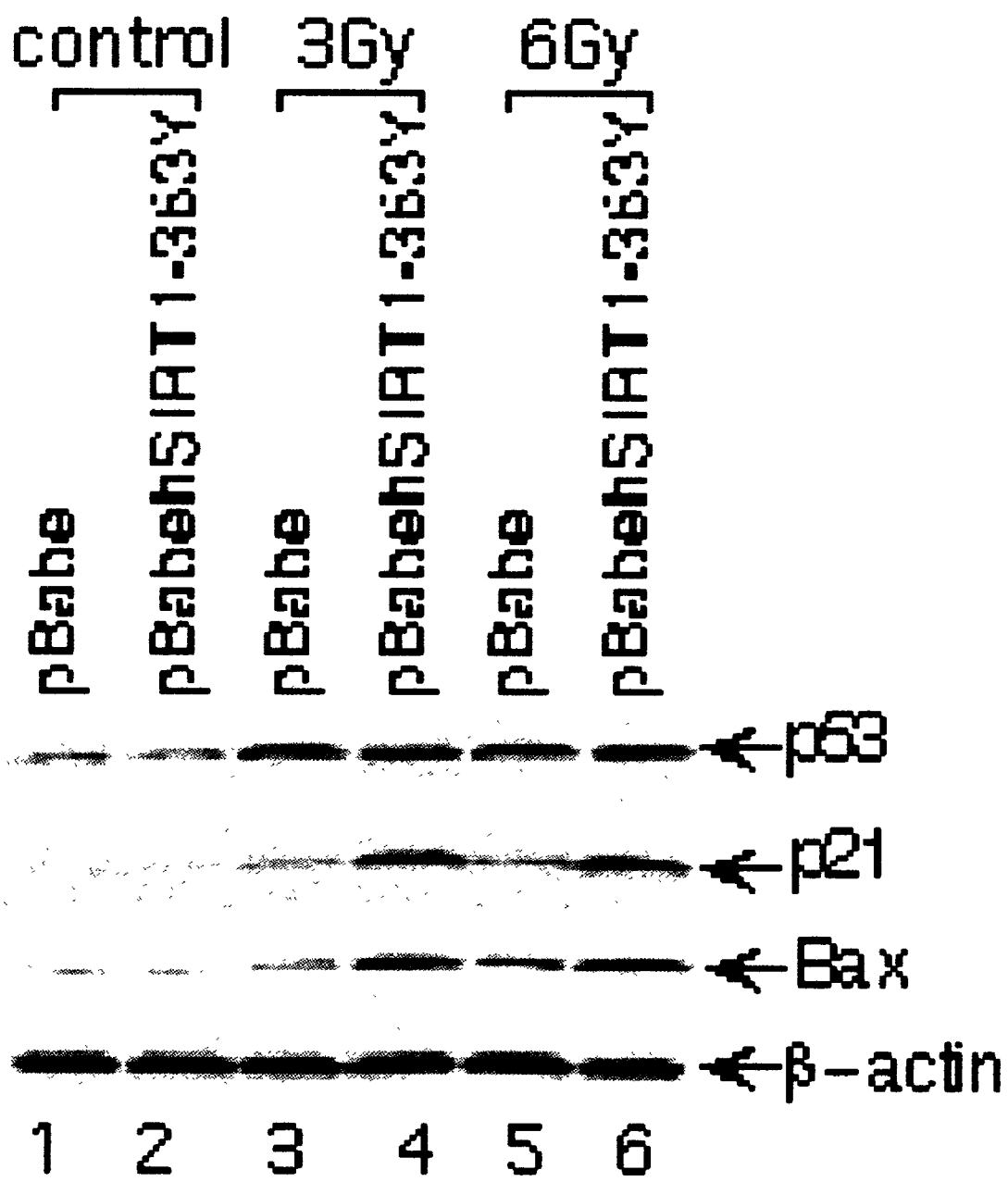
Figure 7D:
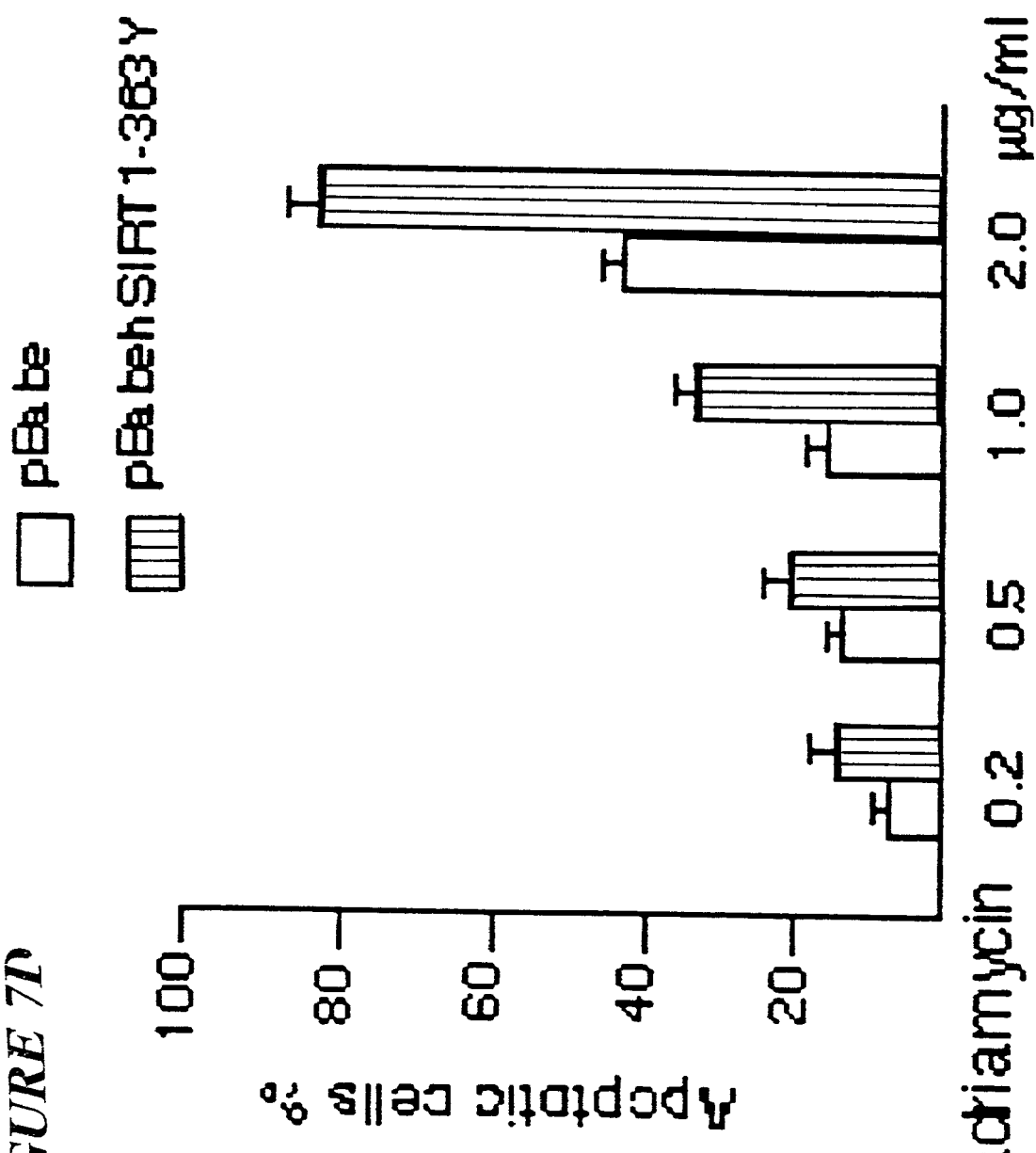
Figure 7E:
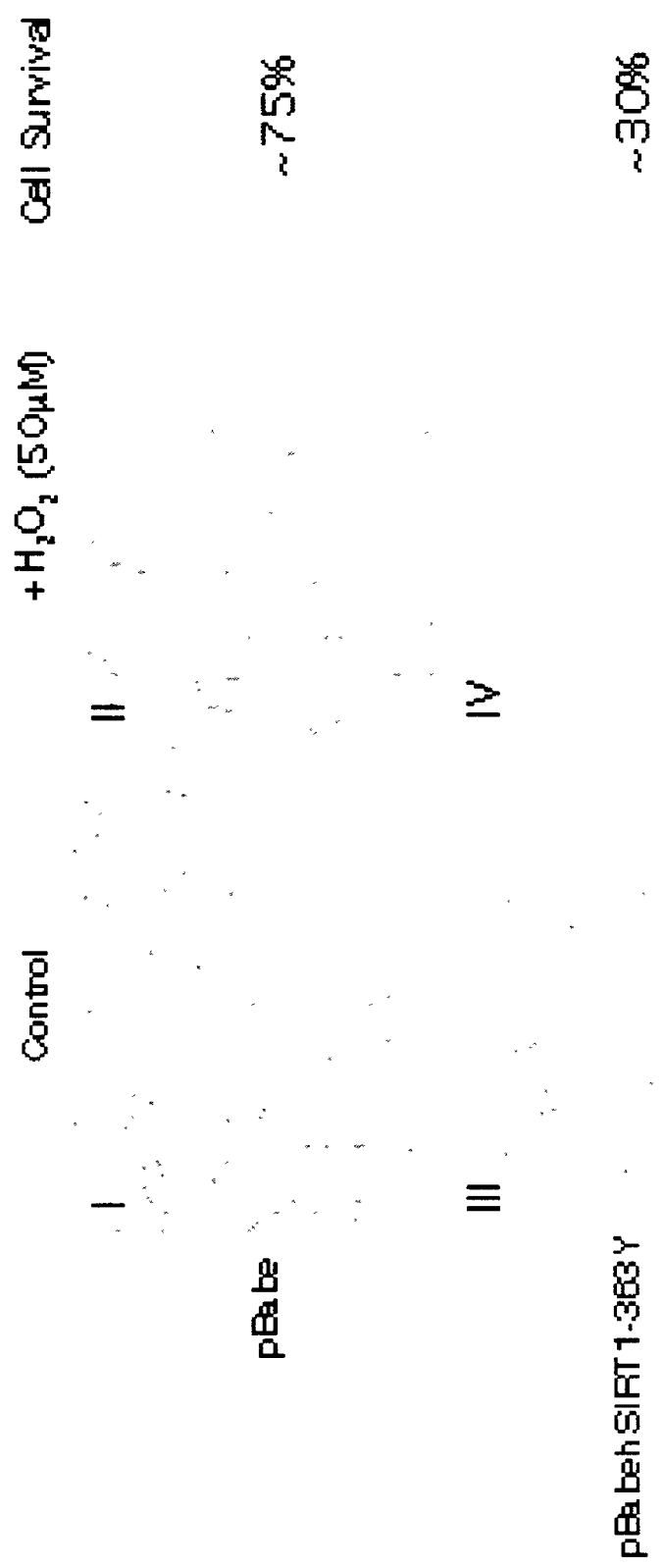

Expression of a Sir2α Point-Mutant Increases the Sensitivity of Cells in the Stress Response To further demonstrate that endogenous Sir2α regulates endogenous p53 under normal conditions, we introduced a Sir2α point-mutant (hSIRT1-363Y), which is functionally-defective in p53 deacetylation (FIG. 2C), into normal human cells. IMR-90 cells were infected with either a pBabe retrovirus empty vector or a pBabe retrovirus containing hSIRT1-363Y, and cultured for a week under pharmacological selection. As indicated in FIG. 7A, the pBabe-hSIRT1-363Y infected cells expressed a significant amount of the mutant protein whereas similar levels of p53 were induced in both types of cells after DNA damage treatment (lanes 3, 4 vs. lanes 1, 2, FIG. 7A). Significantly, the levels of acetylated p53 were strongly enhanced in the pBabe-hSIRT1-363Y-infected cells, indicating that hSIRT1-363Y functions as a dominant negative mutant and inhibits endogenous Sir2α-mediated deacetylation of p53 (lane 4 vs. 3, FIG. 7B). We further test whether hSIRT1-363Y expression has any effect on p53 target genes induced by DNA damage. As indicated in FIG. 7C, both p21 and Bax were induced in the cells after DNA damage, interestingly however, the expression levels of both p21 and Bax in hSIRT1-363Y infected cells were significantly higher than those in mock-infected cells, indicated that hSIRT1-363Y expression abrogates the endogenous Sir2α-mediated repression on p53-dependent transactivation. Moreover, although the IMR-90 cells were susceptible to $H_2O_2$-induced cell death after exposure to 200 μM $H_2O_2$ (FIG. 6D), the cells were relatively resistant to the treatment with a lower concentration of $H_2O_2$ (50 μM) (II vs. I, FIG. 7E). In contrast, hSIRT1-363Y expression led to the cells very sensitive to such a mild treatment (50 μM $H_2O_2$), with less than 30% of the cells surviving (IV vs. III, FIG. 7E). In order to collaborate these results, we also test whether hSIRT1-363Y expression increases the sensitivity of the cells in DNA damage-induced cell death. As shown in FIG. 7D, the pBabe-hSIRT1-363Y infected cells are much more sensitive to DNA damage-induced cell death when the cells were treated with different concentrations of a DNA damage-induced reagent adriamycin.

Taken together, these results suggest that endogenous Sir2α is critically involved in deacetylating p53 as well as regulating p53-mediated biological functions under physiological conditions.

B. Discussion

The present data reveal the existence of a novel p53 regulatory pathway that is controlled by mammalian Sir2α. Sir2α is involved in gene silencing and extension of life span in yeast and *C. elegans* (reviewed in Guarente, 2000; Shore, 2000; Kaeberlein et al., 1999; Tissenbaun and Guarente, 2001). Although the mammalian homolog has also been shown to contain a unique histone deacetylase activity (Imai et al., 2000; Smith et al., 2000), its biological function remains to be elucidated. We show here (i) that p53 strongly binds to mouse Sir2α as well as its human ortholog hSIRT1 both in vitro and in vivo, (ii) that p53 is a substrate for the NAD-dependent deacetylase of mammalian Sir2α, (iii) that the Sir2α-mediated deacetylation antagonizes p53-dependent transcriptional activation and apoptosis, (iv) that the Sir2α-mediated deacetylation of p53 is inhibited by nicotinamide both in vitro and in vivo, (v) that Sir2α specifically inhibits p53-dependent apoptosis in response to DNA damage as well as oxidative stress, but not the p53-independent, Fas-mediated cell death, and (vi) expression of a Sir2α point mutant increases the sensitivity of the cells in response to stress. These results are especially relevant to the multiple regulatory pathways of p53 in vivo and, since the acetylation levels of p53 are stimulated in response to various types of stress, to the role of mammalian Sir2α in stress response.

The Sir2α-Mediated Pathway is Critical for Cells Under Stress

Our study implicates a novel, Mdm2-independent, negative regulatory pathway for p53, which further supports the views that there are multiple pathways in cells for tight regulation of p53 function (Prives and Hall, 1999; Appella and Anderson, 2000). In normal cells, Mdm2 is the major negative regulator for p53, and Mdm2-mediated repression appears sufficient to downregulate p53 activity. Interestingly, while no obvious effect by Sir2α expression was observed in cells at normal conditions, Sir2α becomes critical in protecting cells from apoptosis when cells were either treated by DNA damage or under oxidative stress (FIG. 6). Therefore, we propose that this Sir2α-mediated pathway is critical for cell survival when the p53 negative control mediated by Mdm2 is severely attenuated in response to DNA damage or other types of stress.

In this regard, p53 is often found as latent forms and the levels of p53 protein are very low in unstressed cells, mainly due to the tight regulation by Mdm2 through functional inhibition and protein degradation mechanisms (reviewed in Freedman et al., 1999). However, in response to DNA damage, p53 is phosphorylated at multiple sites at the N-terminus. These phosphorylation events contribute to p53 stabilization and activation by preventing binding with Mdm2 (reviewed in Appella and Anderson, 2000; Shieh et al., 1997). Mdm2 itself is also phosphorylated by ATM during DNA damage response, and this modification attenuates its inhibitory potential on p53 (Maya et al., 2001). Furthermore, while p53 is strongly stabilized and highly acetylated in stressed cells, acetylation of the C-terminal multiple lysine sites may occupy the same sites responsible for Mdm2-mediated ubiquitination (Rodriguez et al., 2000; Nakamura et al., 2000), and the highly acetylated p53 can not be effectively degraded by Mdm2 without deacetylation (Ito et al., 2001). Thus, in contrast to unstressed cells, the main p53 negative regulatory pathway mediated by Mdm2 is severely blocked at several levels in response to DNA damage (Maya et al., 2001). Under these circumstances, the Sir2α-mediated regulation may become a major factor in controlling p53 activity, making it possible for cells to adjust the p53 activity for DNA repair before committing to apoptosis.

Attenuation of p53-Mediated Transactivation by Sir2α

Earlier studies indicated that p53-mediatded transcriptional activation is sufficient and also absolutely required for its effect on cell growth arrest, while both transactivation-dependent and -independent pathways are involved in p53-mediated apoptosis (reviewed in Prives and Hall, 1999). However, there is now growing evidence showing that p53 can effectively induce apoptosis by activating pro-apoptotic genes in vivo (reviewed in Nakano and Vousden, 2001; Yu et al., 2001). Thus, tight regulation of p53-mediated transactivation is critical for its effect on both cell growth and apoptosis (Chao et al., 2000; Jimenez et al., 2000).

Recent studies indicate that the intrinsic histone deacetylase activtiy of Sir2α is essential for its mediated functions (reviewed in Gurante, 2000). Reversible acetylation was originally identified in histones, however, accumulating evidence indicates that transcriptional factors are also functional targets of acetylation (reviewed in Sterner and Berger, 2000; Kouzarides, 2000). Thus, the transcriptional attenuation mediated by histone deacetylases may act through the effects on both histone and non-histone transcriptional factors (Sterner and Berger, 2000; Kuo and Allis, 1998). Interestingly, microarray surveys for transcriptional effects of Sir2 in yeast revealed that Sir2 appears to repress amino acid biosynthesis genes, which are not located at traditional "silenced" loci (Bernstein et al., 2000). Thus, in addition to silencing (repression) at telomeres, mating type loci and ribosomal DNA (reviewed in Guarente, 2000; Shore, 2000), Sir2 may also be targeted to specific endogenous genes for transcriptional regulation in yeast.

In fact, there are at least seven different Sir2 homologs present in mammalian cells, but only mouse Sir2α and human SIRT1 are truly orthologs to yeast Sir2 based on the amino acid sequence homology and protein structure similarity (Frye, 1999, 2000; Imai et al., 2000). In addition, mouse SIR2L2 and SIR2L3 (or Human SIRT2 and SIRT3), are cytoplasmic proteins (Yang et al., 2000; Perrod et al., 2001). We have found that neither human SIRT5 nor SIRT6 binds to, or has any effect in deacetylating p53 in vivo (FIG. 2C), further supporting the specificity of the regulation of p53 by mammalian Sir2α. Furthermore, in contrast to the yeast counterpart Sir2, the mouse Sir2α protein does not co-localize with nucleoli, telomeres or centromeres by co-immunofluorescence assay, indicating that this protein is not associated with the most highly tandemly repeated DNA in the mouse genome. The immunostaining pattern of Sir2α indicates that mammalian Sir2α is, similar to HDAC1, broadly localized in the nucleus, further supporting the notion that mammalian Sir2α may be recruited to specific target genes for transcriptional regulation in vivo.

Our results suggest that mammalian Sir2α inhibits p53-mediated apoptosis through attenuation of the transcriptional activation potential of p53. Our study also predicts that other cellular factors may use a similar mechanism to recruit Sir2 family proteins for TSA-insensitive transcriptional regulation in mammalian cells.

Novel Implications for Cancer Therapy

Inactivation of p53 functions has been well documented as a common mechanism for tumorigenesis (Vogelstein et al., 2000). Many cancer therapy drugs have been designed based on either reactivating p53 functions or inactivating p53 negative regulators. Since p53 is strongly activated in response to DNA damage mainly through attenuation of the Mdm2-mediated negative regulatory pathway (Maya et al., 2001), many DNA damage-inducing drugs such as etoposide are very effective antitumor drugs in cancer therapy (reviewed in Chresta and Hickman, 1996; Lutzker and Levine, 1996). Based on our results that the maximum induction of p53 acetylation in normal cells requires both types of deacetylase inhibitors in addition to DNA damage, there are at least three different p53-negative regulatory pathways in mammalian cells. Interestingly, inhibitors for HDAC-mediated deacetylases, including sodium butyrate, TSA, SAHA and others, have been also proposed as antitumor drugs (reviewed in Marks, et al., 2001; Butler et al., 2000; Yoshida et al., 1995). Thus, we envision as one embodiment of this invention propose that the combining DNA damage drugs, HDAC-mediated deacetylase inhibitors, and Sir2α-medidated deacetylase inhibitors, in cancer therapy for maximally activating p53.

In contrast to PID/HDAC1-mediated p53 regulation (Luo et al., 2000), our results have shown that mammalian Sir2α-mediated effect on p53 is NAD-dependent, indicating that this type of regulation is closely linked to cellular metabolism (reviewed in Guarente 2000; Campisi, 2000). In fact, null mutants of NPT1, a gene that functions in NAD synthesis, show phenotypes similar to that of Sir2 mutants in silencing (Smith et al., 2000) and in life extension in response to caloric restriction in yeast (Lin et al, 2000). Thus, metabolic rate may play a role in Sir2α-mediated regulation of p53 function and, perhaps, modulate the sensitivity of cells in p53-dependent apoptotic response.

C. Experimental Procedures

Plasmids and Antibodies

To construct Sir2α expression constructs, the full-length cDNA was subcloned from pET28a-Sir2α (Imai et al., 2000) into pcDNA3 or pBabepuro vector. Site-directed mutation was generated in the plasmid pRS305-Sir2α using the Gene Edit system (Promega). To construct the human SIRT1 expression construct, DNA sequences corresponding to the full-length hSIRT1 (Frye, 1999) were amplified by PCR from Marathon-Ready Hela cDNA (Clontech), and initially subcloned into pcDNA3.1/V5-His-Topo vector (Invitrogen), and then subcloned with a Flag-tag into a pCIN4 vector for expression (Gu et al., 1999). To prepare the Sir2α antibody that can recognize both human and mouse Sir2α, we made a polyclonal antibody against the highly conserved C-terminus of Sir2α. DNA sequences corresponding to this region (480–737) were amplified by PCR and subcloned into pGEX-2T (Pharmacia). α-Sir2α antisera were raised in rabbits against the purified GST-Sir2α (480–737) fusion protein (Covance), and further affinity-purified on both protein-A and antigen columns. By western blot analysis and immunofluorescent staining, this antibody can detect both mouse Sir2α and human SIRT1 proteins.

In vitro p53 Deacetyltion Assay

The Flag-tagged Sir2α cells were established and expanded in DMEM medium, and cell extracts were prepared essentially as previously described (Luo et al., 2000; Gu et al., 1999). The proteins were purified under a very high stringency condition (300 mM NaCl and 0.5% NP-40). The eluted proteins were resolved by a SDS-PAGE gel and analyzed by colloidal blue staining (Novex). Acetylated GST-p53 was prepared by p53 acetylation assay as previously described (Gu and Roeder, 1997) and further purified on glutathione-Sepharose (Luo et al., 2000). The $^{14}$C-labeled acetylated p53 (2.5 μg) was incubated with purified Sir2α (10 ng) at 30° C. for 1 hr either in the presence of 50 μM NAD or as indicated. The reactions were performed in a buffer containing 50 mM Tris-HCl (pH 9.0), 50 mM NaCl, 4 mM MgCl$_2$, 0.5 mM DTT, 0.2 mM PMSF, 0.02% NP-40 and 5% glycerol. The reactions were resolved on SDS-PAGE and analyzed by Coomassie blue staining and autoradiography.

Virus Infection and Stress Response

All MEF cells were maintained in DMEM medium supplemented with 10% fetal bovine serum, and the IMR-90 cells were maintained in Eagle's minimal essential medium supplemented with 10% fetal bovine serum and non-essential amino acids. The virus infection and selection were essentially as described previously (Ferbeyre et al., 2000). After one-week selection, the cells were either frozen for stock or immediately used for further analysis. About 500,000 MEF cells were plated on a 10-cm dish 24 hr before treatment. The cells were then exposed to etoposide (20 μm) for 12 hr. After treatment, the cells were washed with PBS and fed with normal medium. Another 36 hrs later, the cells were stained with PI and analyzed by flow cytometric analysis for apoptotic cells (SubG1) according to DNA content. In case of the Fas-mediated apoptosis assay, the cells were treated with actinomycin D (0.25 μg/ml) and Fas antibody (100 ng/ml) as previously described (Di Cristofano, et al., 1999). In the case of oxidative stress response, the IMR-90 cells were treated with H$_2$O$_2$ (50 to 200 μM) for 24 hrs.

Detecting Acetylation Levels of p53 in Cells

The cells (human lung carcinoma cell lines H460 (wild-type p53) and H1299 (p53-null), human colon carcinoma HCT116 (wild-type p53), mouse embryonal carcinoma cell line F9 (wild-type p53), mouse embryonic fibroblast MEFs or others) were maintained in DMEM medium supplemented with 10% fetal bovine serum. For DNA damage response, about 1 million cells were plated on a 10-cm dish 24 hr before treatment. The cells were then exposed to etoposide (20 μM) and or other drugs (0.5 μM of TSA, 5 mM of nicotinamide, and 50 μM of ALLN) as indicated for 6 hr. After treatment, the cells were harvested for western blot analysis. The rabbit polyclonal antibody specific for p300-mediated acetylated p53[α-p53(Ac)-C] was raised and purified against the acetylated human p53 C-terminal peptide [p53 (Ac)-C: H-S55GQSTSRH55LMF-OH (5=acetylated Lysine)] as described before (Luo et al., 2000). In the case of cotransfection assays testing for p53 acetylation levels, H1299 cells were transfected with 5 μg of CMV-p53 plasmid DNA, 5 μg of CMV-p300 plasmid DNA, and 10 μg of pcDNA3-Sir2α plasmid DNA as indicated. 24 hr after the transfection, the cells were lysed in a Flag-lysis buffer (50 mM Tris, 137 mM NaCl, 10 mM NaF, 1 mM EDTA, 1% Triton X-100 and 0.2% Sarkosyl, 1 mM DTT, 10% glycerol, pH 7.8) with fresh proteinase inhibitors, 10 μM TSA and 5 mM nicotinamide (Sigma). The cell extracts were resolved by either 8% or 4–20% SDS-PAGE gels (Novex) and analyzed by western blot with α-p53(Ac)-C and α-p53(DO-1).

REFERENCES

Appella, E., Anderson, C. W. (2000). Signaling to p53: breaking the posttranslational modification code. Pathol Biol (Paris) 48, 227–245.

Avantaggiati, M. L., Ogryzko, V., Gardner, K., Giordano, A., Levine, A. S., Kelly, K. Recruitment of p300/CBP in p53-dependent signal pathways. (1997). Cell 89, 1175–1184.

Bernstein, B. E., Tong, J. K., Schreiber, S. L. (2000). Genomewide studies of histone deacetylase function in yeast. Proc. Natl. Acad. Sci. USA, 97, 13708–13713.

Butler, L. M., Agus, D. B., Scher, H. I., Higgins, B., Rose, A., Cordon-Cardo, C., Thaler, H. T., Rifkind, R. A., Marks, P. A., Richon, V. M. (2000). Suberoylanilide hydroxamic acid, an inhibitor of histone deacetylase suppresses the growth of prostate cancer cells in vitro and in vivo. Cancer Res 60, 5165–5170.

Campisi, J. (2000). Aging, chromatin, and food restriction-connecting the dots. Science 289, 2062–2063.

Chen, Q. M., Liu, J., Merrett, J. B. (2000). Apoptosis or senescence-like growth arrest: influence of cell-cycle position, p53, p21 and bax in H$_2$O$_2$ response of normal human fibroblasts. Biochem. J. 347, 543–551.

Chao, C., Saito, S., Kang, J., Anderson, C. W., Appella, E., Xu, Y. (2000) p53 transcriptional activity is essential for p53-dependent apoptosis following DNA damage. EMBO J. 19, 4967–4975.

Chresta, C. M., Hickman, J. A. (1996). Oddball p53 in testicular tumors. Nat Med 2, 745–746.

Di Cristofano, A., Kotsi, P., Peng, Y. F., Cordon-Cardo, C., Elkon, K. B., Pandolfi, P. P. (1999). Impaired Fas response and autoimmunity in Pten+/− mice. Science 285, 2122–2125.

Ferbeyre, G., de Stanchina, E., Querido, E., Baptiste, N., Prives, C., Lowe, S. W. (2000). PML is induced by oncogenic ras and promotes premature senescence. Genes Dev. 14, 2015–2027.

Finnin, M. S., Donigian, J. R., Pavletich, N. P. (2001). Structure of the histone deacetylase SIRT2. Nat Struct Biol. 8, 621–625.

Freedman, D. A., Wu, L., Levine, A. J. (1999). Functions of the MDM2 oncoprotein. Cell Mol Life Sci 55, 96–107.

Frye, R. A. (1999). Characterization of five human cDNAs with homology to the yeast SIR2 gene: Sir2-like proteins (sirtuins) metabolize NAD and may have protein ADP-ribosyltransferase activity. Biochem. Biophys. Res. Commun. 260, 273–279.

Frye, R. A. (2000). Phylogenetic classification of prokaryotic and eukaryotic Sir2-like proteins. Biochem. Biophys. Res. Commun. 273, 793–798.

Gu, W., Malik, S., Ito, M., Yuan, C. X., Fondell, J. D., Zhang, X., Martinez, E., Qin, J., Roeder, R. G. (1999). A novel human SRB/MED-containing cofactor complex, SMCC, involved in transcription regulation. Mole. Cell 3, 97–108.

Gu, W., and Roeder, R. G. (1997). Activation of p53 sequence-specific DNA binding by acetylation of the p53 C-terminal domain. Cell 90, 595–606.

Gu, W., Shi, X. L., Roeder, R. G. (1997). Synergistic activation of transcription by CBP and p53. Nature 387, 819–823.

Guarente, L. (2000). Sir2 links chromatin silencing, metabolism, and aging. Genes Dev. 14, 1021–1026.

Guo, A., Salomoni, P., Luo, J., Shih, A., Zhong, S., Gu, W., Pandolfi, P. P. (2000). The function of PML in p53-dependent apoptosis. Nature Cell Biol. 2, 730–736.

Hollstein, M., Rice, K., Greenblatt, M. S., Soussi, T., Fuchs, R., Sorlie, T., Hovig, E., Smith-Sorensen, B., Montesano, R., Harris, C. C. (1994). Database of p53 gene somatic mutations in human tumors and cell lines. Nucleic Acids Res 22, 3551–3555.

Imai, S., Armstrong, C. M., Kaeberlein, M., Guarente, L. (2000). Transcriptional silencing and longevity protein Sir2 is an NAD-dependent histone deacetylase. Nature 403, 795–800.

Ito, A., Lai, C., Zhao, X., Saito, S., Hamilton, M., Appella, E., Yao, T. (2001). p300/CBP-mediated p53 acetylation is commonly induced by p53-activating agents and inhibited by MDM2. EMBO J 20, 1331–1340.

Jimenez, G. S., Nister, M., Stommel, J. M., Beeche, M., Barcarse, E. A., Zhang, X. Q., O'Gorman, S., Wahl, G. M. (2000) A transactivation-deficient mouse model provides insights into Trp53 regulation and function. Nature Genetics 26, 37–43.

Juan, L. J., Shia, W. J., Chen, M. H., Yang, W. M., Seto, E., Lin, Y. S., Wu, C. W. (2000). Histone deacetylases specifically down-regulate p53-dependent gene activation. J Biol Chem 275, 20436–20443.

Kaeberlein, M., McVey, M., Guarente, L. (1999). The SIR2/3/4 complex and SIR2 alone promote longevity in *Saccharomyces cerevisiae* by two different mechanisms. Genes Dev 13, 2570–2580.

Kobet, E., Zeng, X., Zhu, Y., Keller, D., Lu, H. (2000) MDM2 inhibits p300-mediated p53 acetylation and activation by forming a ternary complex with the two proteins. Proc Natl Acad Sci USA. 97, 12547–12552.

Kouzarides, T. (2000). Acetylation: a regulatory modification to rival phosphorylation? EMBO J 19, 1176–1179.

Kuo, M. H., Allis, C. D. (1998). Roles of histone acetyl-transferases and deacetylases in gene regulation. Bioessays 20, 615–626.

Landry, J., Slama, J. T., Sternglanz, R. (2000a). Role of NAD(+) in the deacetylase activity of the SIR2-like proteins. Biochem Biophys Res Commun 278, 685–690.

Landry, J., Sutton, A., Tafroy, S. T., Heller, R. C., Stebbins, J., Pillus, L., Sternglanz, R. (2000b). The silencing protein SIR2 and its homologs are NAD-dependent protein deacetylases. Proc. Natl. Acad. Sci. USA 97, 5807–5811.

Levine, A. J. (1997). p53, the cellular gatekeeper for growth and division. Cell 88, 323–331.

Lill, N. L., Grossman, S. R., Ginsberg D., DeCaprio, J., Livingston, D. M. (1997). Binding and modulation of p53 by p300/CBP coactivators. Nature, 387, 823–827.

Lin, S. J., Defossez, P. A., Guarente, L. (2000). Requirement of NAD and SIR2 for life-span extension by calorie restriction in *Saccharomyces cerevisiae*. Science 289, 2126–2128.

Liu, L., Scolnick, D. M., Trievel, R. C., Zhang, H. B., Marmorstein, R., Halazonetis, T. D., Berger, S. L. (1999). p53 sites acetylated in vitro by PCAF and p300 are acetylated in vivo in response to DNA damage. Mol. Cell Biol. 19, 1202–1209.

Lohrum, M. A., Vousden, K. H. (1999). Regulation and activation of p53 and its family members. Cell Growth Differ. 6, 1162–1168.

Luo, J., Su, F., Chen, D., Shiloh, A., Gu, W. (2000). Deacetylation of p53 modulates its effect on cell growth and apoptosis. Nature 408, 377–381.

Lutzker, S. G., Levine, A. J. (1996). A functionally inactive p53 protein in teratocarcinoma cells is activated by either DNA damage or cellular differentiation. Nat Med 2, 804–810.

Marks, P. A., Rifkind, R. A., Richon, V. M., and Breslow, R. (2001) Inhibitors of histone deacetylase are potentially effective anticancer agents. Clin. Cancer Res. 7, 759–760.

Maya, R., Balass, M., Kim, S. T., Shkedy, D., Leal, J. F., Shifman, O., Moas, M., Buschmann, T., Ronai, Z., Shiloh, Y., Kastan, M. B., Katzir, E., Oren, M. (2001) ATM-dependent phosphorylation of Mdm2 on serine 395: role in p53 activation by DNA damage. Genes Dev. 15, 1067–1077.

Migliaccio, E., Giorgio, M., Mele, S., Pelicci, G., Reboldi, P., Pandolfi, P. P., Lanfrancone, L., Pelicci, P. G. (1999). The p66shc adaptor protein controls oxidative stress response and life span in mammals. Nature, 402, 309–313.

Min, J., Landry, J., Sternglanz, R., Xu, R. M. (2001). Crystal structure of a SIR2 homolog-NAD complex. Cell 105, 269–279.

Muth, V., Nadaud, S., Grummt, I., Voit, R. (2001). Acetylation of TAF(I)68, a subunit of TIF-IB/SL1, activates RNA polymerase I transcription. EMBO J 20, 1353–1362.

Nakamura, S., Roth, J. A., Mukhopadhyay, T. (2000). Multiple lysine mutations in the C-terminal domain of p53 interfere with MDM2-dependent protein degradation and ubiquitination. Mol Cell Biol 20, 9391–9398.

Nakano, K., Vousden, K. (2001) PUMA, a Novel Proapoptotic Gene, Is Induced by p53. Molecular Cell 7, 683–694.

Pearson, M., Carbone, R., Sebastiani, C., Cioce, M., Fagioli, M., Saito, S., Higashimoto, Y., Appella, E., Minucci, S., Pandolfi, P. P., Pelicci, P. G. (2000). PML regulates p53 acetylation and premature senescence induced by oncogenic Ras. Nature, 406, 207–210.

Perrod, S., Cockell, M. M., Laroche, T., Renauld, H., Ducrest, A. L., Bonnard, C., Gasser, S. M. (2001). A cytosolic NAD-dependent deacetylase, Hst2p, can modulate nucleolar and telomeric silencing in yeast. EMBO J 20, 197–209.

Prives, C., and Hall, P. A. (1999). The p53 pathway. Pathol J. 187, 112–126.

Rodriguez, M. S., Desterro, J. M., Lain, S., Lane, D. P., Hay, R. T. (2000). Multiple C-terminal lysine residues target p53 for ubiquitin-proteasome-mediated degradation. Mol Cell Biol 20, 8458–8467.

Sakaguchi, K., Herrera, J. E, Saito, S., Miki, T., Bustin, M., Vassilev, A., Anderson, C. W., Appella, E. (1998). DNA damage activates p53 through a phosphorylation-acetylation cascade. Genes Dev. 12, 2831–2841.

Shieh, S. Y., Ikeda, M., Taya, Y., Prives, C. (1997). DNA damage-induced phosphorylation of p53 alleviates inhibition MDM2. Cell 91, 325–334.

Shore, D. (2000). The Sir2 protein family: A novel deacetylase for gene silencing and more. Proc. Natl. Acad. Sci. USA, 97, 14030–14032.

Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., Boeke, J. D. (2000). A phylogenetically conserved NAD-dependent protein deacetylase activity in the Sir2 protein family. Proc. Natl. Acad. Sci. USA, 97, 6658–6663.

Sterner, D. E., Berger, S. L. (2000). Acetylation of histones and transcription-related factors. Microbiol Mol Biol 64, 435–459.

Tanner, K. G., Landry, J., Sternglanz, R., Denu, J. M. (2000); Silent information regulator 2 family of NAD-dependent histone/protein deacetylases generates a unique product, 1-O-acetyl-ADP-ribose. Proc. Natl. Acad. Sci. USA, 97, 14178–14182.

Tanny, J. C., Moazed, D. (2001). Coupling of histone deacetylation to NAD breakdown by the yeast silencing protein Sir2: Evidence for acetyl transfer from substrate to an NAD breakdown product. Proc. Natl. Acad. Sci. USA 98, 415–420.

Tissenbaum, H. A., Guarente, L. (2001). Increased dosage of a sir-2 gene extends lifespan in *Caenorhabditis elegans*. Nature 410, 227–230.

Vaziri, H., West, M. D., Allsopp, R. C., Davison, T. S., Wu, Y. S., Arrowsmith, C. H., Poirier, G. G., Benchimol, S. (1997) ATM-dependent telomere loss in aging human diploid fibroblasts and DNA damage lead to the post-translational activation of p53 protein involving poly (ADP-ribose) polymerase. EMBO J. 16, 6018–6033.

Vogelstein, B., Lane, D., and Levine, A. J. (2000). Surfing the p53 network. Nature 408, 307–310.

Yang, Y., Chen, Y., Zhang, C., Nimmakayamu, M., Ward, D., Weissman, S. (2000). Cloning and characterization of two mouse genes with homology to the yeast Sir2 gene. Genomics 69, 355–369.

Yin, Y., Terauchi, Y., Solomon, G. G., Aizawa, S., Rangarajan, P. N., Yazaki, Y., Kadowaki, T., Barrett, J. C. (1998). Involvement of p85 in p53-dependent apoptotic response to oxidative stress. Nature, 391, 707–710.

Yoshida, M., Horinouchi, S., Beppu, T. (1995). Trichostatin A and trapoxin: novel chemical probes for the role of histone acetylation in chromatin structure and function. BioEssays 5, 423–430.

Yu, A., Fan, H., Lao, D., Bailey, A. D., and Weiner, A. M., (2000). Activation of p53 or loss of the Cockayne syndrome group B repair protein causes metaphase fragility of human U1, U2, and 5S genes. Mol. Cell 5, 801–810.

Yu, J., Zhang, L., Hwang, P., Kinzler, K., and Vogelstein, B. (2001). PUMA Induces the Rapid Apoptosis of Colorectal Cancer Cells. Molecular Cell 7, 673–682.

What is claimed is:

1. A method for treating a subject afflicted with cancer comprising administering to the subject a therapeutically effective amount of (i) vitamin $B_3$ or nicotinamide, (ii) Trichostatin A and (iii) Etoposide.

2. The method of claim 1, wherein the subject is human.

3. The method of claim 1, wherein the method comprises administering to the subject a therapeutically effective amount of (i) vitamin $B_3$, (ii) Trichostatin A and (iii) Etoposide.

4. The method of claim 1, wherein the method comprises administering to the subject a therapeutically effective amount of (i) nicotinamide, (ii) Trichostatin A and (iii) Etoposide.

5. A method for inducing the death of a cell comprising contacting the cell with (i) vitamin $B_3$ or nicotinamide, (ii) Trichostatin A and (iii) Etoposide.

6. The method of claim 5, wherein the cell is a human cell.

7. The method of claim 5, wherein the method comprises administering to the subject a therapeutically effective amount of (i) vitamin $B_3$, (ii) Trichostatin A and (iii) Etoposide.

8. The method of claim 5, wherein the method comprises administering to the subject a therapeutically effective amount of (i) nicotinamide, (ii) Trichostatin A and (iii) Etoposide.

* * * * *